(12) United States Patent
Zhang et al.

(10) Patent No.: US 10,302,645 B2
(45) Date of Patent: May 28, 2019

(54) MATERIALS AND METHODS FOR DIAGNOSIS, PROGNOSIS AND ASSESSMENT OF THERAPEUTIC/PROPHYLACTIC TREATMENT OF PROSTATE CANCER

(71) Applicant: ABBOTT MOLECULAR INC., Des Plaines, IL (US)

(72) Inventors: Ying Zhang, Wilmette, IL (US); Larry Morrison, Oro Valley, AZ (US); Ekaterina Pestova, Glenview, IL (US); Irina Sokolova, Villa Park, IL (US)

(73) Assignee: Abbott Molecular Inc., Des Plaines, IL (US)

(*) Notice: Subject to any disclaimer, the term of this patent is extended or adjusted under 35 U.S.C. 154(b) by 0 days.

(21) Appl. No.: 15/443,499

(22) Filed: Feb. 27, 2017

(65) Prior Publication Data

US 2017/0184599 A1 Jun. 29, 2017

Related U.S. Application Data

(62) Division of application No. 13/721,081, filed on Dec. 20, 2012, now Pat. No. 9,617,601.

(60) Provisional application No. 61/582,212, filed on Dec. 30, 2011.

(51) Int. Cl.
| C12Q 1/6886 | (2018.01) |
| G01N 33/574 | (2006.01) |
| G01N 33/487 | (2006.01) |
| C12Q 1/6827 | (2018.01) |

(52) U.S. Cl.
CPC ..... *G01N 33/57434* (2013.01); *C12Q 1/6886* (2013.01); *G01N 33/48721* (2013.01); *C12Q 1/6827* (2013.01); *C12Q 2600/158* (2013.01); *G01N 2333/47* (2013.01)

(58) Field of Classification Search
None
See application file for complete search history.

(56) References Cited

U.S. PATENT DOCUMENTS

| 5,491,224 | A | 2/1996 | Bittner et al. |
| 5,658,730 | A | 8/1997 | McGill et al. |
| 5,756,696 | A | 5/1998 | Gray et al. |
| 6,262,242 | B1 | 7/2001 | Steck et al. |
| 6,482,795 | B1 | 11/2002 | Steck et al. |
| 6,613,510 | B2 | 9/2003 | Jenkins et al. |
| 7,037,667 | B1 | 5/2006 | Afar et al. |
| 7,217,795 | B2 | 5/2007 | Steck et al. |
| 7,425,414 | B2 | 9/2008 | Coignet |
| 7,718,369 | B2 | 5/2010 | Tomlins et al. |
| 9,617,601 | B2 | 4/2017 | Zhang et al. |
| 2003/0087248 | A1* | 5/2003 | Morrison ............... C12Q 1/6841 435/6.16 |
| 2003/0091994 | A1 | 5/2003 | Jenkins et al. |
| 2003/0165895 | A1 | 9/2003 | Czerniak et al. |
| 2005/0252773 | A1 | 11/2005 | McBride et al. |
| 2007/0059747 | A1* | 3/2007 | Bastian ............... C12Q 1/6841 435/6.14 |
| 2009/0069194 | A1 | 3/2009 | Ramakrishnan |
| 2011/0037643 | A1 | 2/2011 | Torin et al. |

FOREIGN PATENT DOCUMENTS

| JP | 2000511433 | 9/2000 |
| JP | 2008536493 | 9/2008 |
| WO | WO93/18186 | 9/1993 |
| WO | WO96/17958 | 6/1996 |
| WO | WO97/46702 | 12/1997 |
| WO | WO98/45479 | 10/1998 |
| WO | WO03/012067 | 2/2003 |
| WO | WO2006/107854 | 10/2006 |
| WO | WO2008/121132 | 10/2008 |
| WO | WO2009/144460 | 12/2009 |
| WO | WO2010/056993 | 5/2010 |
| WO | WO2010/099577 | 9/2010 |

OTHER PUBLICATIONS

Zhou et al. The American Journal of Surgical Pathology. 2002. 26(7):926-931. (Year: 2002).*
Aitchison A., et al., "RASSFIA Promoter Methylation is Frequently Detected in Both Pre-malignant and Non-malignant Microdissected Prostatic Epithelial Tissues," The Prostate, 2007, vol. 67 (6), pp. 638-644.
Ananthanarayanan V., et al., "Alpha-methylacyl-CoA Racemase (AMACR) Expression in Normal Prostatic Glands and High-grade Prostatic Intraepithelial Neoplasia (HGPIN): Association with Diagnosis of Prostate Cancer," The Prostate, 2005, vol. 63 (4), pp. 341-346.
Ananthanarayanan V., et al., "Alteration of Proliferation and Apoptotic Markers in Normal and Premalignant Tissue Associated with Prostate Cancer," BMC Cancer, 2006, vol. 6, pp. 73.
Andy Choo K.H., ed., In Situ Hybridization Protocols: Methods in Molecular Biology, vol. 33, Humana Press Inc., 1994, Table of Contents.
Balakumaran B.S., et al., "MYC Activity Mitigates Response to Rapamycin in Prostate Cancer through Eukaryotic Initiation Factor 4E-Binding Protein 1-Mediated Inhibition of Autophagy," Cancer Research, 2009, vol. 69 (19), pp. 7803-7810.

(Continued)

*Primary Examiner* — Joseph G. Dauner
(74) *Attorney, Agent, or Firm* — Melissa E. Kolom; Casimir Jones, S.C.

(57) ABSTRACT

A method to detect prostate cancer comprising contacting a sample of prostate cells from the patient with a set of detectably labeled probes under hybridization conditions and determining the presence of chromosomal abnormalities in prostate tumor tissue, PIN (intra-epithelial neoplasia), histologically benign tissue and benign prostatic hyperplasia (BPH); a method to combine immunofluorescence and FISH (IF-FISH) to facilitate the assessment of chromosomal abnormalities; a set of probes; and a kit comprising the set of probes and instructions for diagnosing prostate cancer in a patient.

9 Claims, 5 Drawing Sheets

(56) References Cited

OTHER PUBLICATIONS

Bova G.S., et al., "Homozygous Deletion and Frequent Allelic Loss of Chromosome 8p22 Loci in Human Prostate Cancer," Cancer Research, 1993, vol. 53 (17), 3869-3873.
Campos-Fernandes J.L., et al., "Prostate Cancer Detection Rate in Patients with Repeated Extended 21-sample Needle Biopsy," European Urology, 2009, vol. 55 (3), pp. 600-606.
Carter N.P., "Methods and Strategies for Analyzing Copy Number Variation Using DNA Microarrays," Nature Genetics, 2007, vol. 39 (Suppl. 7), pp. S16-S21.
Chandran U.R., et al., "Differences in Gene Expression in Prostate Cancer, Normal Appearing Prostate Tissue Adjacent to Cancer and Prostate Tissue from Cancer Free Organ Donors," BMC Cancer, 2005, vol. 5, pp. 45.
Dong J.T., "Prevalent Mutations in Prostate Cancer," Journal of Cellular Biochemistry, 2006, vol. 97 (3), pp. 433-447.
Emmert-Buck M.R., et al., "Allelic Loss on Chromosome 8p12-21 in Microdissected Prostatic Intraepithelial Neoplasia," Cancer Research, 1995, vol. 55 (14), pp. 2959-2962.
Herrick J., et al., "Quantifying Single Gene Copy Number by Measuring Fluorescent Probe Lengths on Combed Genomic DNA,"Proceedings of the National Academy of Sciences, 2000, vol. 97 (1), pp. 222-227.
International Search Report and Written Opinion for Application No. PCT/US2012/070746, dated Mar. 13, 2013, 14 pages.
Ishkanian A.S, et al., "Array CGH as a Potential Predictor of Radiocurability in Intermediate Risk Prostate Cancer," Acta Oncologica, 2010, vol. 49 (7), pp. 888-894.
Jenkins R.B., et al., "Detection of C-Myc Oncogene Amplification and Chromosomal Anomalies in Metastatic Prostatic Carcinoma by Fluorescence in Situ Hybridization," Cancer Research, 1997, vol. 57 (3), pp. 524-531.
Jiang Z., et al., "Using an AMACR (P504S)/34betaE12/p63 Cocktail for the Detection of Small Focal Prostate Carcinoma in Needle Biopsy Specimens," American Journal of Clinical Pathology, 2005, vol. 123 (2), pp. 231-236.
Kagan J., et al., "Homozygous Deletions at 8p22 and 8p21 in Prostate Cancer Implicate These Regions as the Sites for Candidate Tumor Suppressor Genes," Oncogene, 1995, vol. 11 (10), pp. 2121-2126.
Kallioniemi A., et al., "Comparative Genomic Hybridization for Molecular Cytogenetic Analysis of Solid Tumors," Science, 1992, vol. 258 (5083), pp. 818-821.
Kallioniemi O.P., et al., "ERBB2 Amplification in Breast Cancer Analyzed by Fluorescence in Situ Hybridization," Proceedings of the National Academy of Sciences, 1992, vol. 89 (12), pp. 5321-5325.
Korac P., et al., "Application of the FICTION Technique for the Simultaneous Detection of Immunophenotype and Chromosomal Abnormalities in Routinely Fixed, Paraffin Wax Embedded Bone Marrow Trephines," Journal of Clinical Pathology, 2005, vol. 58 (12), pp. 1336-1338.
Kumar J., et al., "Detection of Differential Gene Copy Number Using Denaturing High Performance Liquid Chromatography," Journal of Biochemical and Biophysical Methods, 2005, vol. 64 (3), pp. 226-234.
Liu Z., et al., "Simple Copy Number Determination with Reference Query Pyrosequencing (RQPS)," Cold Spring Harbor Protocols, 2010, vol. 2010 (9), 10 pages.
Mehrotra J., et al., "Quantitative, Spatial Resolution of the Epigenetic Field Effect in Prostate Cancer," The Prostate, 2008, vol. 68 (2), pp. 152-160.
Meigs J.B., et al., "Interpreting Results of Prostate-specific Antigen Testing for Early Detection of Prostate Cancer," Journal of General Internal Medicine, 1996, vol. 11 (9), pp. 505-512.
Morrison, L.E. et al., "Labeling Fluorescence In Situ Hybridization Probes for Genomic Targets," Methods in Molecular Biology, 2002, vol. 204, pp. 21-40.
Nakayama M., et al., "GSTP1 CpG Island Hypermethylation as a Molecular Biomarker for Prostate Cancer," Journal of Cellular Biochemistry, 2004, vol. 91 (3), pp. 540-552.
Nonn L., et al., "Evidence for Field Cancerization of the Prostate," The Prostate, 2009, vol. 69 (13), pp. 1470-1479.
Olapade-Olaopa E.O., et al., "Malignant Transformation of Human Prostatic Epithelium is Associated with the Loss of Androgen Receptor Immunoreactivity in the Surrounding Stroma," Clinical Cancer Research, 1999, vol. 5 (3), pp. 569-576.
Pinkel D., et al., "Fluorescence in Situ Hybridization with Human Chromosome-Specific Libraries: Detection of Trisomy 21 and Translocations of Chromosome 4," Proceedings of the National Academy of Sciences, 1988, vol. 85 (23), pp. 9138-9142.
Prostate Cancer, Cancer Facts and Figures, 2010, pp. 23-37.
Qian J., et al., "The Extent and Multicentricity of High-grade Prostatic Intraepithelial Neoplasia in Clinically Localized Prostatic Adenocarcinoma," Human Pathology, 1997, vol. 28 (2), pp. 143-148.
Reynolds M.A., "Molecular Alterations in Prostate Cancer," Cancer Letters, 2008, vol. 271 (1), pp. 13-24.
Rigby P.W., et al., "Labeling Deoxyribonucleic Acid to High Specific Activity in Vitro by Nick Translation with DNA Polymerase I," Journal of Molecular Biology, 1977, vol. 113 (1), pp. 113-237.
Rizzi F., et al., "A Novel Gene Signature for Molecular Diagnosis of Human Prostate Cancer by RT-qPCR," PLoS One, 2008, vol. 3 (10), pp. e3617.
Sambrook J., et al., eds., Molecular Cloning: A Laboratory Manual, 3rd Edition, Cold Spring Harbor Laboratory, 2001, Table of Contents.
Santinelli A., et al., "alpha-Methylacyl Coenzyme A Racemase, Ki-67, and Topoisomerase IIalpha in Cystoprostatectomies with Incidental Prostate Cancer," American Journal of Clinical Pathology, 2007, vol. 128 (4), pp. 657-666.
Sato K., et al., "Clinical Significance of Alterations of Chromosome 8 in High-Grade, Advanced, Nonmetastatic Prostate Carcinoma," Journal of the National Cancer Institute, 1999, vol. 91 (18), pp. 1574-1580.
Schouten J.P., et al., "Relative Quantification of 40 Nucleic Acid Sequences by Multiplex Ligation-dependent Probe Amplification," Nucleic Acids Research, 2002, vol. 30 (12), pp. e57.
Service R.F., "Gene Sequencing. The Race for the $1000 Genome," Science, 2006, vol. 311 (5767), pp. 1544-1546.
Shen M.M., et al., "Molecular Genetics of Prostate Cancer: New Prospects for Old Challenges," Genes & Development, 2010, vol. 24 (18), pp. 1967-2000.
Shen W.H., et al., "Essential Role for Nuclear PTEN in Maintaining Chromosomal Integrity," Cell, 2007, vol. 128 (1), pp. 157-170.
Shendure J., et al., "Advanced Sequencing Technologies: Methods and Goals," Nature Reviews. Genetics, 2004, vol. 5 (5), pp. 335-344.
Shi S.R., et al., "Antigen Retrieval Technique Utilizing Citrate Buffer or Urea Solution for Immunohistochemical Demonstration of Androgen Receptor in Formalin-Fixed Paraffin Sections," Journal of Histochemistry & Cytochemistry, 1993, vol. 41 (11), pp. 1599-1604.
Sokolova I., et al., "Chromosomal Biomarkers for Detection of Human Papillomavirus Associated Genomic Instability in Epithelial Cells of Cervical Cytology Specimens," Journal of Molecular Diagnostics, 2007, vol. 9 (5), pp. 604-611.
Thompson I.M., et al., "Prevalence of Prostate Cancer Among Men with a Prostate-specific Antigen Level < or =4.0 ng per Milliliter," New England Journal of Medicine, 2004, vol. 350 (22), pp. 2239-2246.
Tijssen P., "Overview of Principles of Hybridization and the Strategy of Nucleic Acid Probe Assays, Hybridization with Nucleic Acid Probes" in: Laboratory Techniques in Biochemistry and Molecular Biology, vol. 24, Chapter 2, Van der Vliet P.C., ed., Elsevier Publisher, 1993, pp. 19-78.
Veltri R.W., et al., "Ability to Predict Metastasis Based on Pathology Findings and Alterations in Nuclear Structure of Normal-appearing and Cancer Peripheral Zone Epithelium in the Prostate," Clinical Cancer Research, 2004, vol. 10 (10), pp. 3465-3473.

(56) References Cited

OTHER PUBLICATIONS

Vlaeminck-Guillem V., et al., "Urinary Prostate Cancer 3 Test: Toward the Age of Reason?," Urology, 2010, vol. 75 (2), pp. 447-453.

Vogelstein B., et al., "Digital PCR," Proceedings of the National Academy of Sciences, 1999, vol. 96 (16), pp. 9236-9241.

Yoshimoto M., et al., "FISH Analysis of 107 Prostate Cancers Shows that PTEN Genomic Deletion is Associated with Poor Clinical Outcome," British Journal of Cancer, 2007, vol. 97 (5), pp. 678-685.

Yu Y.P., et al., "Gene Expression Alterations in Prostate Cancer Predicting Tumor Aggression and Preceding Development of Malignancy," Journal of Clinical Oncology, 2004, vol. 22 (14), pp. 2790-2799.

Zhang., et al., Proceedings of the 101 st Annual Meeting of the American Association for Cancer Research, Apr. 17-21, 2010, 70 (8 Suppl): Abstract 823.

Qian J., et al., "Chromosomal Anomalies in Prostatic Intraepithelial Neoplasia and Carcinoma Detected by Fluorescence in Situ Hybridization." Cancer Research, Nov. 15, 1995, 55, 5408-5414.

\* cited by examiner

Diagnostic Cutoff Ranges

| Probes and Abnormalities | Parameter | Tumor ROI | | | Benign ROI | | |
|---|---|---|---|---|---|---|---|
| | | Cut-off | Spec | Sens | Cut-off | Spec | Sens |
| MYC/LPL %Gain | Upper Range of Cutoff | 22 | 100 | 61.8 | 19 | 100 | 35.3 |
| | Chosen Cutoff | 14 | 96.2 | 79.4 | 18 | 80.8 | 58.8 |
| | Lower Range of Cutoff | 12 | 73.1 | 85.3 | 12 | 73.1 | 58.8 |
| CEP8 %Abnorm | Upper Range of Cutoff | 40 | 100 | 64.7 | 34 | 100 | 29.4 |
| | Chosen Cutoff | 34 | 88.5 | 94.1 | 32 | 76.9 | 64.7 |
| | Lower Range of Cutoff | 26 | 61.6 | 97.1 | 25 | 61.6 | 76.5 |
| PTEN %loss | Upper Range of Cutoff | 54 | 100 | 20.6 | 28 | 80.8 | 64.7 |
| | Chosen Cutoff | 44 | 80.8 | 58.8 | 26 | 80.8 | 70.6 |
| | Lower Range of Cutoff | 22 | 65.4 | 64.7 | 22 | 65.4 | 82.3 |
| MYC/CEP8 %Gain | Upper Range of Cutoff | 18 | 100 | 61.8 | 18 | 100 | 23.5 |
| | Chosen Cutoff | 16 | 88.8 | 76.5 | 16 | 61.5 | 70.6 |
| | Lower Range of Cutoff | 10 | 61.5 | 88.2 | 9 | 61.5 | 70.6 |

FIG. 3

| Parameter | AUC |
|---|---|
| PTEN%Loss – Benign ROI | 0.827 |
| CEP7%Abnorm – Benign ROI | 0.845 |
| MYC%Gain – Benign ROI | 0.846 |
| CEP8%Gain – Benign ROI | 0.871 |
| 4 Probes Combination – Benign ROI | 0.917 |
| 4 Probes Combination-Tumor ROI | 0.960 |

Figure 5

| Probe Set | Probe combination | PTEN%loss | CEP7%abnormal | MYC%gain | CEP8%gain | Sens | Spec |
|---|---|---|---|---|---|---|---|
| Upper Range of cutoff | PTEN%loss, CEP7%abnormal, MYC%gain, CEP8%gain | 33 | 29 | 50 | 34 | 82.35% | 88.46% |
| Probe set1 | PTEN%loss, CEP7%abnormal, MYC%gain, CEP8%gain | 33 | 28 | 35 | 34 | 88.20% | 84.60% |
| Lower Range of cutoff | PTEN%loss, CEP7%abnormal, MYC%gain, CEP8%gain | 29 | 24 | 2 | 32 | 100% | 61.54% |

MATERIALS AND METHODS FOR DIAGNOSIS, PROGNOSIS AND ASSESSMENT OF THERAPEUTIC/PROPHYLACTIC TREATMENT OF PROSTATE CANCER

CROSS-REFERENCE TO RELATED APPLICATION(S)

This is a divisional of U.S. patent application Ser. No. 13/721,081, filed on Dec. 20, 2012, which claims priority to U.S. Provisional Patent Application No. 61/582,212, filed on Dec. 30, 2011, the entire contents of all of which are fully incorporated herein by reference.

TECHNICAL FIELD

The present disclosure relates to methods of diagnosis, prognosis and assessment of the therapeutic or prophylactic treatment of cancer, in particular prostate cancer, the detection of phenotypic and genotypic abnormalities, immunofluorescence, and in situ hybridization, as well as a set of probes and a kit useful in such methods.

BACKGROUND

Prostate cancer is the most common malignancy in men, and, after lung cancer, the second leading cause of death in men. There were an estimated 217,730 new cases in 2010 resulting in 32,050 deaths (www.cancer.gov). The majority of tumors are confined to the prostate. Others are clinically localized to the peri-prostatic area but extend through the prostatic capsule and may involve seminal vesicles. The remaining tumors are metastatic.

The absence of reliable diagnostic markers that enable early and accurate detection of tumors when they are confined to the prostate, as well as prognostic markers that enable prediction of disease progression, is a fundamental problem in the management of prostate cancer. Early detection and diagnosis of prostate cancer currently relies on digital rectal examination (DRE), prostate-specific antigen (PSA) measurement, transrectal ultrasonography (TRUS), and transrectal needle biopsy (TRNB). The leading diagnostic approach employs a combination of DRE and measurement of serum PSA; however, this approach has major limitations. Detection of an elevation in the level of PSA is more sensitive than specific (Thompson et al., NEJM 350: 2239-2246 (2004)). Consequently, more men are unnecessarily subjected to needle biopsy due to PSA screening and, unfortunately, the focal nature of prostate cancer results in needle biopsy sampling errors with false negative rates of 15-30% during diagnosis (Campos-Fernandes et al., Eur. Urol. 55: 600-609 (2009)). Out of the approximately 1.2 million patients who undergo prostate biopsy each year in the U.S., 70-80% receive negative results but cannot be reassured because a cancer might have been missed by sampling error (Nonn et al., Prostate 69: 1470-1479 (2009)). Therefore, repeat biopsies (second, third or fourth) are necessary because of continuous elevated PSA levels (Campos-Fernandes et al. (2009), supra).

Besides PSA, other markers and methods have been identified. For example, the measurement of the level of amplification of the HER-2/neu gene by fluorescence in situ hybridization (FISH) has been disclosed to be a method of determining the severity of prostate cancer (Int'l Pat. App. Pub. No. WO 1998/045479). The determination of the presence of an amplified 8q24.1-24.2 chromosome band segment has been disclosed to be a method of diagnosing prostate cancer progression (U.S. Pat. No. 5,658,730). The determination of the loss of the 8p21-22 locus, a gain of chromosome 8, and an additional increase of the copy number of c-myc relative to the centromere copy number has been disclosed to be a method of prognosticating prostate cancer (U.S. Pat. No. 6,613,510). The determination of the hybridization pattern of a set of chromosomal probes comprising a probe to the 8p locus, such as 8p21-22, and a probe to the 8q24 locus and correlating the hybridization pattern with prostate cancer diagnosis also has been disclosed (U.S. Pat. App. Pub. No. 2003/0091994). A gain of 8q24 (c-myc) and a loss of heterozygosity of 8p21-22 (LPL) (Bova et al., Cancer Res. 53: 3869-3873 (1993); Kagan et al., Oncogene 11: 2121-2126 (1995); and Emmert-Buck et al., Cancer Res. 55: 2959-2962 (1995)) and 10q23 (PTEN) (Yoshimoto et al., Br. J. Cancer 97(5): 678-685 (Sep. 3, 2007; epub Aug. 14, 2007) also has been described. Testing for the loss of heterozygosity at one or more loci on one or more of chromosomes 1-22 has been disclosed as a method of detecting a cell with a neoplastic or preneoplastic phenotype (U.S. Pat. App. Pub. No. 2003/0165895). The detection of an increase in the level of expression of the 20P1F12/TMPRSS2 gene has been disclosed as a method of identifying prostate cancer (U.S. Pat. No. 7,037,667). The detection of a break in the sequence of human chromosome 12q24 at the SMRT gene locus using FISH has been disclosed as a method of determining the likelihood of prostate cancer metastasis (U.S. Pat. No. 7,425,414). The determination of the level of a constituent such as PTEN RNA has been disclosed as a method for evaluating the presence of prostate cancer (Int'l Pat. App. Pub. No. WO 2008/121132). The detection of an ACSL3-ETS gene fusion has been disclosed as a method of diagnosing prostate cancer (Int'l Pat. App. Pub. No. WO 2009/144460). The detection of the presence of a gene fusion having a 5' portion from a transcriptional regulatory region of a TMPRSS2 gene and a 3' portion from an ERG, ETV1 or ETV4 gene has been disclosed as a method of identifying prostate cancer (U.S. Pat. No. 7,718,369), as well as predicting recurrence, progression and metastatic potential (Int'l Pat. App. Pub. No. WO 2010/056993). The detection of the over-expression of PITX2 has been disclosed as a method for diagnosing the presence or risk of prostate cancer (Int'l Pat. App. Pub. No. WO 2010/099577). The identification of an increased level of a nucleic acid or polypeptide selected from OCT3/4, Nanog, Sox2, c-myc, If4, keratin 8, and uPAR has been disclosed as a method of identifying a prostate carcinoma (In'tl Pat. App. Pub. No. 2011/037643).

In addition to the above, prostate cancer "field effect" has been studied by several groups. Using digital image analysis, researchers have identified subtle changes of nuclear morphology in the histologically benign tissue adjacent to prostate cancer (Qian et al., Hum. Pathol. 28: 143-148 (1997); and Veltri et al., Clin. Cancer Res. 10: 3465-3473 (2004)). Using cDNA microarrays, the difference of gene expression profile was reported between adjacent normal tissue of prostate cancer and normal tissue obtained from organ donors (Chandran et al., BMC Cancer 5(1): 45 (2005); Yu et al., J. Clin. Oncol. 22(14): 2790-2799 (2004); and Rizzi et al., PLoS ONE 3(10): e3617 (2008)). Using immunohistochemistry, protein expression changes of multiple biomarkers were noticed in near and distant normal and high-grade prostatic intra-epithelial neoplasia (HGPIN) glands. These markers include Mcm-2 and Ki67 (Ananthanarayanan et al., BMC Cancer 6: 73 (2006); Santinelli et al., Am. J. Clin. Pathol. 128(4): 657-666 (2007)), α-methylacyl-CoA racemase (AMACR) (Santinelli et al. (2007), supra; and Ananthanarayanan et al., Prostate 63(4): 341-346 (2005)), and androgen receptor (AR) (Olapade-Olaopa et al., Clin. Cancer Res. 5(3): 569-576 (1999)), etc. Using laser capture micro-dissection and quantitative methylation-specific PCR, field effect for gene silencing through hypermethylation in prostate carcinogenesis was also found by multiple groups (Mehrothra et al., Prostate 68(2): 152-160 (2008); and Aitchison et al., Prostate 67(6): 638-644 (2007)). The genes include GSTP1, APC, RASSF1A, HIN-1 and RARb2.

In view of the foregoing, there remains a need for more reliable and informative diagnostic and prognostic methods in the management of prostate cancer. The present disclosure seeks to provide a set of markers, as well as methods of use and a kit comprising the set of markers, for the diagnosis, prognosis, and the assessment of the therapeutic or prophylactic treatment of cancer, in particular prostate cancer. This and other objects and advantages, as well as inventive features, will become apparent from the detailed description provided herein.

SUMMARY

A method of detecting prostate cancer in a patient is provided. Genomic abnormalities in a prostate tumor (malignancy; designated herein "tumor region of interest (ROI)") or an adjacent, apparently benign, area of a prostate (designated herein "benign ROI"), such as in one or more tissue sections of a prostate, are identified and assayed in accordance with the method. In one embodiment, the method comprises contacting a sample of prostate cells from the patient with a set of detectably labeled probes comprising a locus-specific probe for MYC, a locus-specific probe for phosphatase and tensin homolog (PTEN), a centromeric probe for chromosome 8, and a centromeric probe for chromosome 7 under hybridization conditions and determining the presence of chromosomal abnormalities, wherein a MYC % gain (% gain is % of cells with MYC>2 signals) of greater than 35 (with a range of 2 to 50), a PTEN % loss (% loss is % of cells with <2 signals) of greater than 33 (with a range of 29 to 33), a chromosome 8% gain (% gain is % of cells with >2 signals) of greater than 34 (with a range of 32 to 34), and a chromosome 7% abnormal (% abnormal is % of cells with >2 or <2 signals) greater than 28 (with a range of 24 to 29) in a sample of prostate cells from a tumor region of interest (ROI) or a benign ROI of the prostate of the patient indicates that the patient has prostate cancer.

In another embodiment, the method comprises contacting a sample of prostate cells from the patient with a set of detectably labeled probes comprising a locus-specific probe for MYC, a locus-specific probe for lipoprotein lipase (LPL), a locus-specific probe for PTEN, and a centromeric probe for chromosome 8 under hybridization conditions and determining the presence of chromosomal abnormalities. A MYC/LPL % gain (% gain is % of cells with MYC/LPL>1) of greater than 14 (with a range of 12 to 22), a chromosome 8% abnormal (% abnormal is % of cells with >2 or <2 signals) of greater than 34 (with a range of 26 to 40), a PTEN % loss (% loss is % of cells with <2 signals) of greater than 44 (with a range of 22 to 54), or a MYC/chromosome 8% gain (% gain is % of cells with MYC/chromosome 8>1) greater than 16 (with a range of 10 to 18) in a sample of prostate cells from a tumor region of interest (ROI) of the prostate of the patient indicates that the patient has prostate cancer. Cut-offs of combined "MYC/LPL % Gain or CEP8% Abnorm or PTEN % Loss or MYC/CEP8% Gain" for tumor ROI FISH parameters were chosen in the region of target performance: the quadrant between 97.1% sensitivity and 96.2% specificity. A MYC/LPL % gain of greater than 18 (with a range of 12 to 19), a chromosome 8% abnormal of greater than 32 (with a range of 25 to 34), a PTEN % loss of greater than 26 (with a range of 22 to 28), or a MYC/chromosome 8% gain greater than 16 (with a range of 9 to 18) in a sample of prostate cells from a benign ROI of the prostate of the patient indicates that the patient has prostate cancer. Cut-offs of combined "MYC/LPL % Gain or CEP8% Abnorm or PTEN % Loss or MYC/CEP8% Gain" for benign ROI FISH parameters were chosen in the region of target performance: the quadrant between 80.8% sensitivity and 82.4% specificity.

The sample of prostate cells can be a section of the prostate of the patient. The section can be formalin-fixed and paraffin-embedded and placed on a microscope slide. Prior to determining the presence of chromosomal abnormalities, the method can further comprise morphologically assessing the section and identifying at least one tumor ROI, at least one benign ROI, or at least one tumor ROI and at least one benign ROI. Alternatively, prior to determining the presence of chromosomal abnormalities, the method can further comprise assessing the section by immunofluorescence and identifying at least one tumor ROI. Assessing the section by immunofluorescence can comprise contacting the section with a detectably labeled anti-α-methylacyl-CoA racemase (AMACR) antibody and detecting over-expression of AMACR, wherein over-expression of AMACR in a region of the section indicates the presence of a tumor ROI. Prior to assessing the section by immunofluorescence, the method can further comprise treating the section with heat-induced epitope retrieval.

A set of probes is also provided. In one embodiment, the set of probes comprises a locus-specific probe for MYC, a locus-specific probe for PTEN, a centromeric probe for chromosome 8, and a centromeric probe for chromosome 7, wherein the set of probes optionally further comprises an anti-AMACR antibody, which can be detectably labeled. In another embodiment, the set of probes comprises a locus-specific probe for MYC, a locus-specific probe for LPL, a locus-specific probe for PTEN, and a centromeric probe for chromosome 8. The set of probes optionally further comprises an anti-AMACR antibody, which can be detectably labeled.

A kit is also provided. In one embodiment, the kit comprises (a) a set of probes that enables diagnosis of prostate cancer in a patient, wherein the set of probes comprises a locus-specific probe for MYC, a locus-specific probe for PTEN, a centromeric probe for chromosome 8, and a centromeric probe for chromosome 7, and (b) instructions for diagnosing prostate cancer in a patient, wherein the instructions comprise determining in a sample of prostate cells obtained from the patient the presence of chromosomal abnormalities. A MYC % gain (% gain is % of cells with MYC>2 signals) of greater than 35 (with a range of 2 to 50), a PTEN % loss (% loss is % of cells with <2 signals) of greater than 33 (with a range of 29 to 33), a chromosome 8% gain (% gain is % of cells with >2 signals) of greater than 34 (with a range of 32 to 34), and a chromosome 7% abnormal (% abnormal is % of cells with >2 or <2 signals) greater than 28 (with a range of 24 to 29) in a sample of prostate cells from a tumor region of interest (ROI) or a benign ROI of the prostate of the patient indicates that the patient has prostate cancer. In another embodiment, the kit comprises (a) a set of probes that enables diagnosis of prostate cancer in a patient, wherein the set of probes comprises a locus-specific probe for MYC, a locus-specific probe for LPL, a locus-specific probe for PTEN, and a centromeric probe for chromosome 8 and (b) instructions for diagnosing prostate cancer in a patient, wherein the instructions comprise determining in a sample of prostate cells obtained from the patient the presence of chromosomal abnormalities. A MYC/LPL % gain (% gain is % of cells with MYC/LPL>1) of greater than 14 (with a range of 12 to 22), a chromosome 8% abnormal (% abnormal is % of cells with >2 or <2 signals) of greater than 34 (with a range of 26 to 40), a PTEN % loss (% loss is % of cells with <2 signals) of greater than 44 (with a range of 22 to 54), or a MYC/chromosome 8% gain (% gain is % of cells with MYC/chromosome 8>1) greater than 16 (with a range of 10 to 18) in a sample of prostate cells from a tumor region of interest (ROI) of the prostate of the patient indicates that the patient has prostate cancer. A MYC/LPL % gain of greater than 18 (with a range of 12 to 19), a chromosome 8% abnormal of greater than 32 (with a range of 25 to 34), a PTEN % loss of greater than 26 (with a range of 22 to 28), or a MYC/chromosome 8% gain greater than 16 (with a range of 9 to 18) in a sample of prostate cells from a benign ROI of the prostate of the patient indicates that the patient has prostate cancer. The kit can further comprise instructions for morphologically assessing a section of a prostate from a patient and identifying at least one tumor ROI, at least one benign ROI, or at least one tumor ROI and at least one benign ROI prior to determining the presence of chromosomal abnormalities. Alternatively, the kit can further comprise instructions for assessing a section of a prostate from a patient by immunofluorescence and identifying the presence of a tumor ROI prior to determining the presence of chromosomal abnormalities, in which case the kit can further comprise an anti-AMACR antibody, which can be detectably labeled, and the instructions for assessing a section of a prostate from a patient by immunofluorescence can further comprise contacting the section with detectably labeled anti-AMACR antibody and detecting over-expression of AMACR, wherein over-expression of AMACR in a region of the section indicates the presence of a tumor ROI. The instructions can further comprise treating the section with heat-induced epitope retrieval prior to assessing the section of a prostate from a patient by immunofluorescence.

BRIEF DESCRIPTION OF THE FIGURES

FIG. 3 is a table of diagnostic cut-offs for CEP 8% Abnorm, MYC/LPL % Gain, MYC/CEP8% Gain, and PTEN % Loss.

FIG. 5 is a table of diagnostic cut-offs for PTEN % Loss, Cep 7% Abnorm, MYC % Gain, and CEP 8% Gain.

DETAILED DESCRIPTION

Figure 1A:
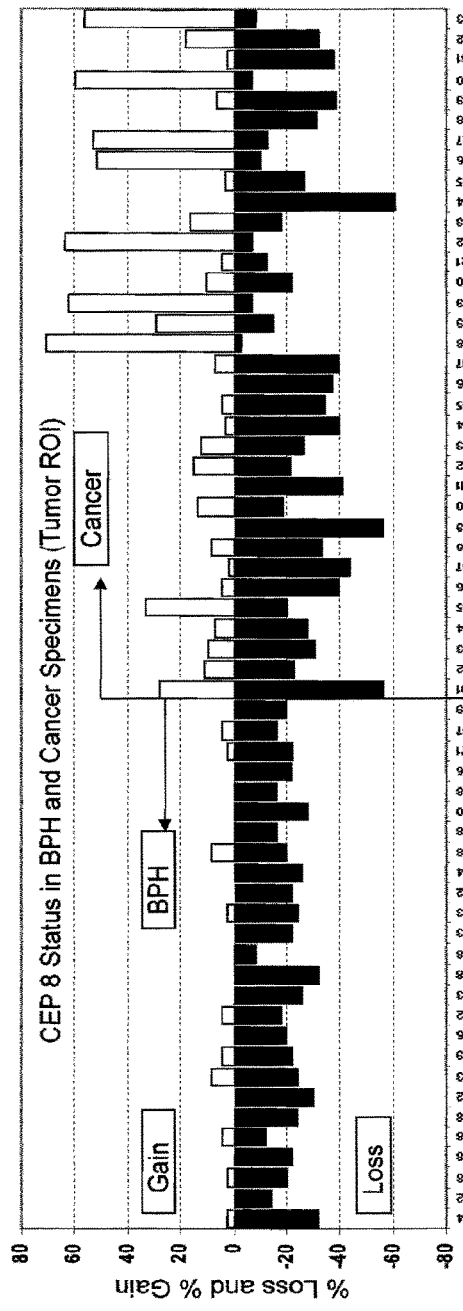
FIG. 1a is a graph of % loss and % gain versus locus of chromosome enumerator probe (CEP) 8 in benign prostatic hyperplasia (BPH) and cancer specimens (tumor region of interest of tumor ROI).
Figure 1B:
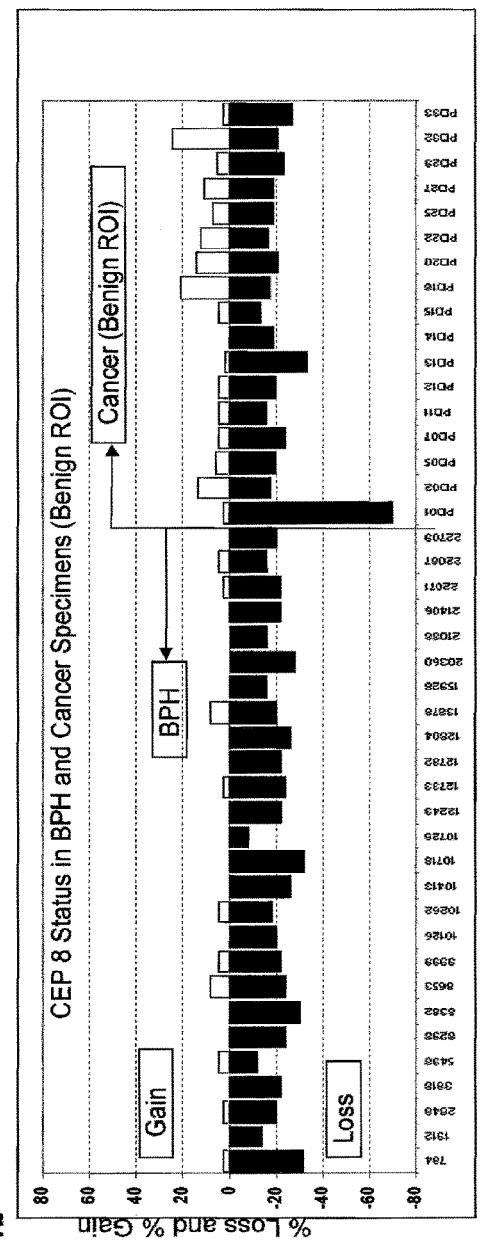
FIG. 1b is a graph of % loss and % gain versus locus for chromosome enumerator probe (CEP) 8 in BPH and cancer specimens (benign ROI).
Figure 2B:
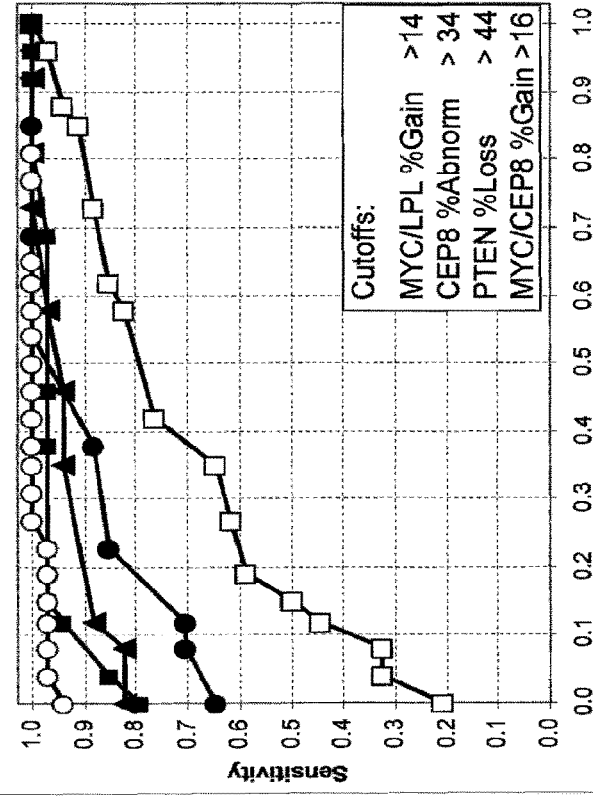
FIG. 2b is a graph of sensitivity vs. 1-specificity (ROC curve) for benign ROI, wherein (■) is the percentage abnormal for chromosome enumerator probe 8 (CEP 8% Abnorm), (▲) is the percentage gain of MYC/lipoprotein lipase (LPL) (MYC/LPL % Gain), (●) is the percentage gain of MYC/CEP 8 (MYC/CEP8% Gain), and (□) is the percentage loss of phosphatase and tensin homolog (PTEN) (PTEN % Loss), and (○) is the combination cut-off of CEP 8, MYC, LPL, and PTEN (4 probes cut-off).
Figure 2A:
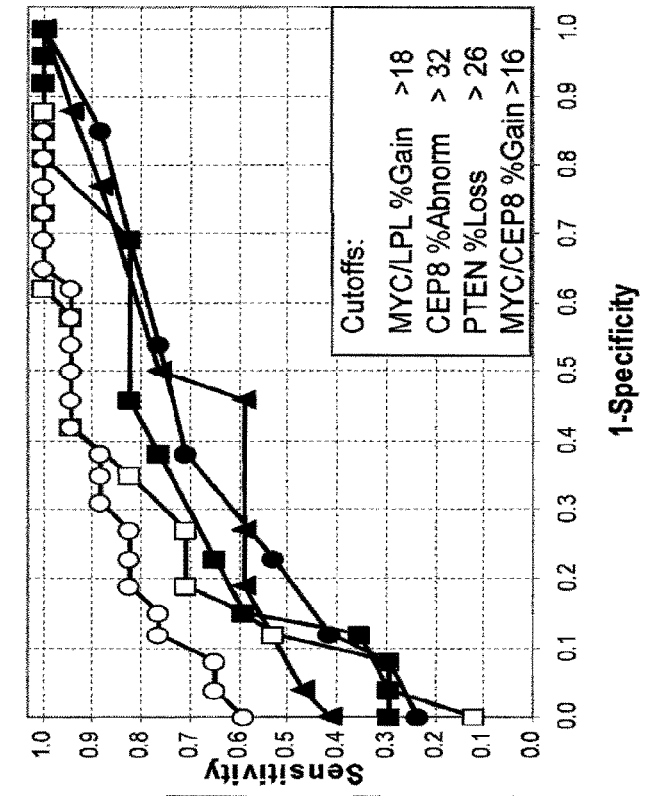
FIG. 2a is a graph of sensitivity vs. 1-specificity (receiver operating characteristic (ROC) curve) for tumor ROI, wherein (■) is the percentage abnormal for chromosome enumerator probe 8 (CEP 8% Abnorm), (▲) is the percentage gain of MYC/lipoprotein lipase (LPL) (MYC/LPL % Gain), (●) is the percentage gain of MYC/CEP 8 (MYC/CEP 8% Gain), and (□) is the percentage loss of phosphatase and tensin homolog (PTEN) (PTEN % Loss), and (○) is the combination cut-off of CEP 8, MYC, LPL, and PTEN (4 probes cut-off).

The present disclosure provides a set of markers, as well as a method of use and a kit comprising the set of markers, for the diagnosis, prognosis, and the assessment of the therapeutic or prophylactic treatment of cancer, in particular prostate cancer. The following terms are relevant to the present disclosure:

"About" refers to approximately a +/−10% variation from the stated value. It is to be understood that such a variation is always included in any given value provided herein, whether or not specific reference is made to it.

"Biomarker," as defined by the National Institutes of Health, is "a characteristic that is objectively measured and evaluated as an indicator of normal biologic processes, pathogenic processes, or pharmacologic responses to a therapeutic intervention."

"Chromosome enumeration probe (CEP)" or "centromeric probe" is any probe that enables the number of specific chromosomes in a cell to be enumerated. A chromosome enumeration probe typically recognizes and binds to a region near to (referred to as "peri-centromeric") or at the centromere of a specific chromosome, typically a repetitive DNA sequence (e.g., alpha satellite DNA). The centromere of a chromosome is typically considered to represent that chromosome, since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals corresponding to the centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes, since the loss of signals for such probes may not always indicate a loss of the entire chromosome. Examples of chromosome enumeration probes include CEP® probes commercially available from Abbott Molecular, Inc., Des Plaines, Ill. (formerly Vysis, Inc., Downers Grove, Ill.).

"Copy number" is a measurement of DNA, whether of a single locus, one or more loci, or an entire genome. A "copy number" of two is "wild-type" in a human (because of diploidy, except for sex chromosomes). A "copy number" of other than two in a human (except for sex chromosomes) deviates from wild-type. Such deviations include amplifications, i.e., increases in copy numbers, and deletions, i.e., decreases in copy numbers and even the absence of copy numbers.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling. The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Locus-specific probe" and "locus-specific identifier (LSI)" may be used interchangeably herein to refer to a probe that selectively binds to a specific locus in a region on a chromosome, e.g., a locus that has been determined to undergo gain/loss in metastasis. A probe can target coding or non-coding regions, or both, including exons, introns, and/or regulatory sequences, such as promoter sequences and the like.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications, whereas a length of about $50-1\times10^5$ nucleotides can be preferred for chromosomal probes and a length of about 25,000 to about 800,000 nucleotides can be preferred for locus-specific probes.

"Prostate cancer" includes all types of prostate cancer, such as adenocarcinoma, small cell carcinoma, squamous cell carcinoma, sarcoma, and transitional cell carcinoma. The majority of prostate cancer (around 95%) is adenocarcinoma. Prostate cancer is distinguished from prostatic intraepithelial neoplasia (PIN, which is further distinguished as low-grade or high-grade), which is a precursor to prostate cancer. Small cell carcinoma and squamous cell carcinoma tend to be very aggressive in nature and do not lead to an increase in prostate-specific antigen (PSA). Transitional cell carcinoma rarely develops in the prostate but derives from primary tumors in the bladder and/or urethra.

"Selectively hybridize to" (as well as "selective hybridization," "specifically hybridize to," and "specific hybridization"), in the context of the present disclosure, refers to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other non-target sequences. A "stringent hybridization" and "stringent hybridization wash conditions" in the context of nucleic acid hybridization (e.g., as in array, Southern hybridization, Northern hybridization, or FISH) are sequence-dependent, and differ under different conditions. An extensive guide to the hybridization of nucleic acids is found in, e.g., Tijssen, *Laboratory Techniques in Biochemistry and Molecular Biology—Hybridization with Nucleic Acid Probes*, Part I, Ch. 2, "Overview of principles of hybridization and the strategy of nucleic acid probe assays," Elsevier, N.Y. (1993) ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids, which have more than 100 complementary residues, on an array or on a filter in a Southern or Northern blot is 42° C. using standard hybridization solutions (see, e.g., Sambrook and Russell, *Molecular Cloning: A Laboratory Manual,* 3rd ed., Vol. 1-3, Cold Spring Harbor Laboratory, Cold Spring Harbor Press, NY (2001)).

"Target sequence," "target region," and "nucleic acid target" refer to a nucleotide sequence that resides at a specific chromosomal location whose loss and/or gain, for example, is being determined.

The terminology used herein is for the purpose of describing particular embodiments only and is not otherwise intended to be limiting.

Methods of Detecting, Diagnosing, Prognosticating, and Monitoring the Efficacy of Therapeutic/Prophylactic Treatment of Prostate Cancer A method of detecting prostate cancer in a patient is provided. In one embodiment, the method comprises contacting a sample of prostate cells from the patient with a set of detectably labeled probes comprising a locus-specific probe for MYC, a locus-specific probe for phosphatase and tensin homolog (PTEN), a centromeric probe for chromosome 8, and a centromeric probe for chromosome 7 under hybridization conditions and determining the presence of chromosomal abnormalities, wherein a MYC % gain (% gain is % of cells with MYC>2 signals) of greater than 35 (with a range of 2 to 50), a PTEN % loss (% loss is % of cells with <2 signals) of greater than 33 (with a range of 29 to 33), a chromosome 8% gain (% gain is % of cells with >2 signals) of greater than 34 (with a range of 32 to 34), and a chromosome 7% abnormal (% abnormal is % of cells with >2 or <2 signals) greater than 28 (with a range of 24 to 29) in a sample of prostate cells from a tumor region of interest (ROI) or a benign ROI of the prostate of the patient indicates that the patient has prostate cancer. In another embodiment, the method comprises contacting a sample of prostate cells, such as a tissue section or cells obtained therefrom, from the patient with a set of detectably labeled probes comprising a locus-specific probe for MYC, a locus-specific probe for lipoprotein lipase (LPL locus), a locus-specific probe for PTEN locus, and a centromeric probe for chromosome 8 under hybridization conditions and determining the presence of chromosomal abnormalities. A MYC/LPL % gain (% gain is % of cells with MYC/LPL>1) of greater than 14 (with a range of 12 to 22), a chromosome 8% abnormal (% abnormal is % of cells with >2 or <2 signals) of greater than 34 (with a range of 26 to 40), a PTEN % loss (% loss is % of cells with <2 signals) of greater than 44 (with a range of 22 to 54), or a MYC/chromosome 8% gain (% gain is % of cells with MYC/chromosome 8>1) greater than 16 (with a range of 10 to 18) in a sample of prostate cells from a tumor ROI of the prostate of the patient indicates that the patient has prostate cancer. A MYC/LPL % gain of greater than 18 (with a range of 12 to 19), a chromosome 8% abnormal of greater than 32 (with a range of 25 to 34), a PTEN % loss of greater than 26 (with a range of 22 to 28), or a MYC/chromosome 8% gain greater than 16 (with a range of 9 to 18) in a sample of prostate cells from a benign ROI of the prostate of the patient indicates that the patient has prostate cancer. Cutoffs of combined "MYC/LPL % Gain or CEP8% Abnorm or PTEN % Loss or MYC/CEP8% Gain" for tumor ROI FISH parameters were chosen in the region of target performance: the quadrant between 97.1% sensitivity and 96.2% specificity. Cutoffs of combined "MYC/LPL % Gain or CEP8% Abnorm or PTEN % Loss or MYC/CEP8% Gain" for benign ROI FISH parameters were chosen in the region of target performance: the quadrant between 80.8% sensitivity and 82.4% specificity.

The set of probes can further comprise one or more of a locus-specific probe for p16 (9p21), TMPRSS2-ERG or ETV1 fusions (21q22; 7p21 locus), a centromeric probe for chromosome 3, a centromeric probe for chromosome 7, a centromeric probe for chromosome 10, and a centromeric probe for chromosome 17. The set of detectably labeled probes can further comprise one or more of a locus-specific probe for cyclin-dependent kinase inhibitor p27Kip1 (4q43), a locus-specific probe for cyclin-dependent kinase 2 (CDK2; 12q13), a locus-specific probe for cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homolog (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12).

A method of histological sample pretreatment and hybridization for prostate cancer is provided. FFPE (Formalin Fixed Paraffin Embedded) histological specimens slides (sections) were baked at 56° C. for 2-24 hrs, then were pretreated two to three times in Hemo-De (Scientific Safety Solvents) or Xyline for 5 to 10 minutes each at room temperature followed by two 1-minute rinses in 100% ethanol at room temperature, incubation in 45% formic acid/0.3% hydrogen peroxide for 15 minutes at room temperature and then rinsed in deionized water for 3-10 minutes. Slides were then incubated in pre-treatment solution (1×SSC, PH6.3) at 80+/−5° C. for 35-50 minutes, rinsed for 3 minutes in deionized water, incubated 22+/−5 minutes in 0.15% pepsin in 0.1N HCl solution at 37° C., and rinsed again for 3 minutes in deionized water. Slides were dehydrated for 1 minute each in 70%, 85%, and 100% ethanol and then air dried. Ten microliters of each respective probe hybridization mix (LSI® buffer, blocking DNA, labeled probes) were added to the specimens, a coverslip applied, and sealed with rubber cement. Slides were codenatured for 5 minutes at 73+/−2° C. and hybridized for 10-24 hours at 37° C. on a ThermoBrite (Vysis/Abbott Molecular, Inc.). Following hybridization, coverslips were removed. The sample could be placed in the wash solution consisting of 0.3×-2×SSC & 0.3%-0.5% NP-40, and the temperature of the sample can be raised to about 73° C. for about 2-5 minutes. Then the support carrying the sample can be either counterstained with a nuclear DNA-binding stain, such as 4',6-diamidino-2-phenylindole (DAPI) either in solution, or upon drying the sample in the dark. In the latter case, the sample is counterstained with about 10 µL DAPI, and a new overslip is placed over the sample. The sample can then be viewed or stored, e.g., at about −20° C.

A method of prostate FFPE slide IF-FISH procedure is provided. For the assay of simultaneous FISH and Immunofluorescence (IF) on the same FFPE prostate solid tumor tissue slides, a specimen pre-treatment/antigen retrieval protocol was developed and optimized for best results on the FFPE tissue for IF-FISH.

The first step of this procedure is antigen retrieval. Bake prostate cancer FFPE slides at 56° C. for two hours to overnight. De-paraffinize by two immersions in Hemo-De for 10 minutes each. Incubate twice in 100% ethanol for two minutes each. Hydrate by placing in 85%, 70%, 50%, and 30% ethanol for two minutes each. Immerse in molecular grade Milli-Q water for five minutes. Pre-heat water bath with Coplin jar containing sodium citrate buffer (Sodium Citrate Buffer: 10 mM sodium citrate, 0.05% Tween 20, pH 6.0) until temperature reaches 96+/−4° C. Incubate for 20-60 minutes. Cool at room temperature for 20-40 minutes on bench. Wash slides for five minutes in Milli-Q water. Rinse once for five minutes in phosphate-buffered saline (PBS).

The second step is the immunoflorescence (IF) with AMACR antibody and Tyramide Signal Amplification Assay (34). Use the Tyramide Solution Assay (TSA) kit and follow the Alexa Fluor 488 TSA (tyramide signal amplification) kit number 2 (Invitrogen, Molecular Probes) following the manufacturer's directions. Endogenous peroxidase activity is blocked by incubation in 3% $H_2O_2$ for 30 minutes at room temperature. Add blocking reagent (100 μL/slide) with incubation in a humidified box for 30 minutes at room temperature. Add 100 μL of diluted AMACR rabbit antibody (diluted in 1% blocking reagent at 1:100) with incubation for one hour at room temperature. Wash slides three times in PBS/0.1% Tween 20 for five minutes each. Dilute the stock HRP conjugate solution 1:100 in 1% blocking solution. A 100 μL volume of this working solution is sufficient to cover a standard 22×22 mm coverslip. Incubate for 30 minutes at room temperature. Wash three times in PBS/0.1% Tween 20 for five minutes each. Wash once in PBS. Add 100 μL of tyramide solution per slide followed by incubation for 10 minutes at room temperature in the dark. Wash slides in PBS for five minutes. Wash slides for five minutes in Milli-Q water. Proceed to FISH.

The third step is FISH assay. Dehydrate slides in alcohol (70%, 85% and 100%, 1 min each), and allow to completely air dry. Add 10 μL of probe solution to each slide, and seal the coverslip over the slide with rubber cement. Co-denature probe and target DNA at 73° C. for five minutes followed by hybridization overnight at 37° C. The sample can be placed in the wash solution consisting of 0.3×-2×SSC and 0.3%-0.5% NP-40, and the temperature of the sample can be raised to about 73° C. for about 2-5 minutes. Then the support carrying the sample can be either counterstained with a nuclear DNA-binding stain, such as 4',6-diamidino-2-phenylindole (DAPI) either in solution, or upon drying the sample in the dark. In the latter case, the sample is counterstained with about 10 μL DAPI, and a new coverslip is placed over the sample. The sample can then be viewed or stored, e.g., at about −20° C.

With regard to all of the above methods, the nature/size of the probe will depend, at least in part, on the method used to determine a particular parameter, e.g., copy number, copy number ratio, or percentage gain of a gene of interest. When an above diagnostic/prognostic method is carried out by in situ hybridization, such as FISH, for example, the probe can be relatively large. When an above diagnostic/prognostic method is carried by another method, the probe can be smaller, even substantially smaller, than the probe used for in situ hybridization, such as FISH, in which case the probe preferably hybridizes to a sequence within the gene of interest.

In view of the above, a probe for detecting a parameter involving MYC, for example, such as the copy number of MYC, a copy number ratio involving MYC, or the percentage gain of MYC, by in situ hybridization, such as FISH, preferably hybridizes to the 8q24 region of chromosome 8, which comprises the MYC gene. The probe also can hybridize to an adjacent region located on the centromeric side of 8q24, an adjacent region located on the telomeric side of 8q24, or both. A preferred probe covers approximately 820 kb, such as 821 kb, of 8q24 and is centered on the MYC gene. A probe for detecting a parameter involving MYC by another method can be smaller, even substantially smaller, than the probe used for in situ hybridization, such as FISH, in which case the probe preferably hybridizes to a sequence within the MYC gene (sequence information is available online from sources such as GenBank (www.ncbi.nlm.nih.gov/genbank) and GeneCards® (www.genecards.org)). "MYC" is used herein to refer to any and all probes that can be used to determine a parameter involving MYC, whether copy number, copy number ratio, percentage gain, and the like, irrespective of the particular method used to determine the parameter.

Like "MYC," "LPL" is used herein to refer to any and all probes that can be used to determine a parameter involving LPL, whether copy number, copy number ratio, percentage gain, and the like, irrespective of the particular method used to determine the parameter. "LPL" includes a probe that preferably hybridizes to the p22 region of chromosome 8, which comprises the LPL gene. The LPL probe also can hybridize to an adjacent region located on the centromeric side of 8p22, an adjacent region located on the telomeric side of 8p22, or both. A preferred LPL probe covers approximately 170 kb of 8p22 and is centered on the LPL gene. "PTEN" is used herein to refer to any and all probes that can be used to determine a parameter involving PTEN, whether copy number, copy number ratio, percentage gain, and the like, irrespective of the particular method used to determine the parameter. "PTEN" includes a probe that preferably hybridizes to the q23 region of chromosome 10, which comprises the PTEN gene. The PTEN probe also can hybridize to an adjacent region located on the centromeric side of 10q23, an adjacent region located on the telomeric side of 10q23, or both. A preferred PTEN probe covers approximately 365-370 kb, such as 368 kb of 10q23 and is centered on the PTEN gene. Adjacent regions of the PTENE gene include STS markers D10S215 on the centromeric side and RH93626 on the telomeric side. The usage of probe designations as explained above applies to methods, probes and kits discussed herein. The same usage applies to other probe designations set forth herein. As indicated above for the MYC gene, sequence information for the genes recited herein is available online from sources such as GenBank (www.ncbi.nlm.nih.gov/genbank) and GeneCards® (www.genecards.org)).

The sample of prostate cells is a section of the prostate of the patient. The sample, such as a tissue section, can be obtained by surgical resection, needle biopsy, trans-urethral resection of prostate (TURP), or a similar technique. The section can be formalin-fixed and paraffin-embedded and placed on a microscope slide. Alternatively, a section preserved by other means, such as freezing, can be used.

Prior to determining the presence of chromosomal abnormalities, the method can further comprise morphologically assessing the section and identifying at least one tumor ROI, at least one benign ROI, or at least one tumor ROI and at least one benign ROI. Alternatively, prior to determining the presence of chromosomal abnormalities, the method can further comprise assessing the section by immunofluorescence and identifying at least one tumor ROI. Assessing the section by immunofluorescence can comprise contacting the section with a detectably labeled anti-α-methylacyl-CoA racemase (AMACR) antibody and detecting over-expression of AMACR, wherein over-expression of AMACR in a region of the section indicates the presence of a tumor ROI. Prior to assessing the section by immunofluorescence, the method can further comprise treating the section with heat-induced epitope retrieval.

The above method can be carried out using any suitable detection method known in the art. Preferably, the above method is carried out using in situ hybridization, such as fluorescent in situ hybridization (FISH). Preferably, each probe is detectably labeled with a distinct label, such as a distinct fluorophore. Alternatively, radiolabeled nucleotide detection (in situ hybridization (ISH)), chromomeric hybridization detection, and the like, as described herein, can be used.

When the above methods are carried out by in situ hybridization, in which each probe is detectably labeled with a distinct label, such as by FISH, in which each probe is labeled with a distinct fluorophore, the methods can be carried out on a sample of prostate cells, which are fresh, such as fresh cells from a biopsy of the prostate (fresh cells can be cultured for 1-3 days and a blocker, such as Colcemid, can be added to the culture to block the cells in metaphase, during which chromosomes are highly condensed and can be visualized), frozen, or fixed (e.g., fixed in formalin and embedded in paraffin), treated (e.g., with RNase and pepsin) to increase accessibility of target nucleic acid (e.g., DNA) and reduce non-specific binding, and then subjected to hybridization with one or more probes, washing to remove any unbound probes, and detection of hybridized probes. For example, a cell suspension can be applied as a single layer onto a slide, and the cell density can be measured by a light or phase contrast microscope. Cells also can be obtained from other sources, such as bodily fluids, e.g., urine or semen, preserved in fixatives, such as methanol-acetic acid (Carnoy's reagent), and applied to a slide or similar support for microscopic examination and analysis.

Alternatively, a section (approximately 4-6 μm in thickness) of tissue, such as a section of a formalin-fixed, paraffin-embedded (FFPE) sample of prostate tissue, can be mounted onto a slide, such as a SuperFrost Plus positively charged slide (available from ThermoShandon, Pittsburgh, Pa.), baked at 56° C. 2 hours to 24 hours (overnight). For FISH assay, sections are then de-paraffinized by pretreating two to three times in Hemo-De (Scientific Safety Solvents, Keller, Tex.) or Xyline for 5 to 10 minutes each at room temperature, followed by rinsing twice in 100% ethanol at room temperature for one minute each rinse, incubating in 45% formic acid/0.3% hydrogen peroxide for 15 minutes at room temperature, and then rinsing in deionized water for 3-10 minutes. Slides are then incubated in pre-treatment solution (1×SSC, PH6.3) at 80+/−5° C. for 35-50 minutes, rinsed for 3 minutes in deionized water, incubated 22+/−5 minutes in 0.15% pepsin in 0.1N HCl solution at 37° C., and rinsed again for 3 minutes in deionized water. Slides are then dehydrated for 1 minute each in 70%, 85%, and 100% ethanol and then air dried.

Ten microliters of each respective probe hybridization mix (LSI® buffer, blocking DNA, and labeled probes) are added to the specimens, and coverslips are applied and sealed with rubber cement. Slides are codenatured for five minutes at 73+/−2° C. and hybridized for 10-24 hours at 37° C. on a ThermoBrite (Vysis/Abbott Molecular, Inc.). Following hybridization, coverslips are removed. The sample is placed in the wash solution consisting of 0.3×-2×SSC and 0.3%-0.5% NP-40, and the temperature of the sample is raised to about 73° C. for about 2-5 minutes. Then the support carrying the sample can be either counterstained with a nuclear DNA-binding stain, such as 4',6-diamidino-2-phenylindole (DAPI) in solution or upon drying the sample in the dark. In the latter case, the sample is counterstained with about 10 μL DAPI, and a new overslip is placed over the sample. The sample can then be viewed or stored, e.g., at about −20° C.

In this regard, heat-induced epitope retrieval (HIER) can be performed, allowing for simultaneous immunofluorescence and FISH. For the assay of simultaneous FISH and Immunofluorescence (IF) on the same FFPE prostate solid tumor tissue slides, a specimen pre-treatment/antigen retrieval protocol was developed and optimized for best results on the FFPE tissue for IF-FISH.

The first step of this procedure is antigen retrieval. Prostate cancer FFPE slides are baked at 56° C. for 2 hours to overnight. Slides are then de-paraffinized by two immersions in Hemo-De for 10 minutes each. Slides are then incubated in 100% ethanol twice for 2 minutes each time. Slides are hydrated by placing in 85%, 70%, 50%, 30% ethanol for 2 minutes each, and a final 5-minute immersion in molecular grade Milli-Q water. A water bath is pre-heated with a Coplin jar containing sodium citrate buffer (10 mM sodium citrate, 0.05% Tween 20, pH 6.0) until the temperature reaches 96+/−4° C. Slides are then incubated for 20-60 minutes, and cooled at room temperature for 20-40 minutes on the bench. Slides are washed for five minutes in Milli-Q water and rinsed once for five minutes in PBS.

The second step is the immunoflorescence (IF) with AMACR antibody and Tyramide Signal Amplification Assay. The Tyramide Solution Assay (TSA) kit and the Alexa Fluor 488 TSA (tyramide signal amplification) kit number 2 (Invitrogen, Molecular Probes) are used following the manufacturer's directions. Endogenous peroxidase activity is blocked by incubation in 3% $H_2O_2$ for 30 minutes at room temperature. Blocking reagent (100 μL/slide) is added, and the slides are incubated in a humidified box for 30 minutes at room temperature. One hundred microliters of diluted AMACR rabbit antibody (diluted in 1% blocking reagent at 1:100) are added, and the slides are incubated for 1 hour at room temperature. Slides are washed three times for five minutes each in PBS/0.1% Tween 20. Stock HRP conjugate solution is diluted 1:100 in 1% blocking solution. A 100 μL volume of this working solution is sufficient to cover a standard 22×22 mm coverslip. Slides are incubated at room temperature for 30 minutes, and then washed three times in PBS/0.1% Tween 20 for five minutes each wash, followed by one wash in PBS. Tyramide solution (100 μL) is added to each slide, and the slides are incubated at room temperature for ten minutes in the dark. The slides are washed for five minutes in PBS and then washed for five minutes in Milli-Q water.

The third step is FISH assay. Slides are dehydrated in alcohol (70%, 85% and 100%, 1 min each), and allowed to air dry completely. Probe solution (10 μL) is added to each slide, and a coverslip is sealed over the slide with rubber cement. Probe and target DNA are denatured at 73° C. for five minutes followed by hybridization overnight at 37° C. The sample then can be placed in a wash solution consisting of 0.3×-2×SSC and 0.3%-0.5% NP-40, and the temperature of the sample can be raised to about 73° C. for about 2-5 minutes. Then the support carrying the sample can be either counterstained with a nuclear DNA-binding stain, such as 4',6-diamidino-2-phenylindole (DAPI) in solution or upon drying the sample in the dark. In the latter case, the sample is counterstained with about 10 μL DAPI, and a new coverslip is placed over the sample. The sample can then be viewed or stored, e.g., at about −20° C.

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. Preferably, regions of interest on prostate specimen slides are identified by detecting over-expression of α-methylacyl-CoA racemase (AMACR) using IF and an anti-AMACR antibody. Alternatively, cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes, such as propidium iodide or 4,6-diamidino-2-phenylindole dihydrochloride (DAPI), usually following hybridization of probes to their target DNAs. Typically, neoplastic cells harbor nuclei that are enlarged, irregular in shape, and/or show a mottled staining pattern. Propidium iodide, typically used at a concentration of about 0.4 μg/ml to about 5 μg/ml, is a red-fluorescing DNA-specific dye that can be observed at an emission peak wavelength of 614 nm. DAPI, typically used at a concentration of about 125 ng/ml to about 1,000 ng/ml, is a blue fluorescing DNA-specific stain that can be observed at an emission peak wavelength of 452 nm with a DAPI filter at low magnification. In this case, only those cells pre-selected for detection are subjected to counting for chromosomal losses and/or gains. Preferably, pre-selected cells on the order of at least 20, and more preferably at least 30-40, in number are chosen for assessing chromosomal losses and/or gains.

Alternatively, an area evidencing some level of dysplasia or a suspicious lesion can be localized using the DAPI filter at low magnification and thoroughly inspected for the presence of nuclei harboring abnormal copy numbers of any probe. In a normal cell, two copies of a given probe will be detected. In an abnormal cell, more or less copies of a given probe will be detected. Areas with the most significant copy number changes are preferably selected for enumeration. Wherever possible, three abnormal areas are selected and, within each abnormal area, 10 random nuclei are analyzed under high power (64× or 100× objective). Preferably, nuclei are non-overlapping and harbor sufficiently bright signals.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

The copies of MYC (8p24), LPL (8p22), PTEN (10q23), and chromosome 8, alone or in further combination with copies of one or more of p16 (9p21), chromosome 3, chromosome 7, chromosome 10, and chromosome 17 are counted, as well as TMPRSS2-ERG or ETV1 Fusions (21q22; 7p21) and deletions and/or translocations thereof. Additionally, the copies of one or more of p27Kip1 (4q43), CDK2 (12q13), cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homol (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12) are counted.

Thus, such methods comprise contacting a sample of prostate cells obtained from a patient, e.g., a nucleic acid sample, with a set of detectably labeled probes comprising a locus-specific probe for MYC (8p24), a locus-specific probe for LPL (8p22), a locus-specific probe for PTEN (10q23), and a centromeric probe for chromosome 8, alone or in further combination with one or more of a locus-specific probe for p16 (9p21), TMPRSS2-ERG or ETV1 Fusions (21q22; 7p21), a centromeric probe for chromosome 3, a centromeric probe for chromosome 7, a centromeric probe for chromosome 10, and a centromeric probe for chromosome 17, wherein the set of detectably labeled probes can comprise one or more of a locus-specific probe for p27Kip1 (4q43), CDK2 (12q13), cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homol (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12)), under conditions that allow (or promote) the probe to bind selectively with its target nucleic acid sequence and form a stable hybridization complex. Such methods further comprise detecting the formation of the hybridization complex and counting the number of hybridization complexes. In view of the number of hybridization complexes comprising MYC (8p24), LPL (8p22), PTEN (10q23), and chromosome 8, alone or in further combination with the number of hybridization complexes of one or more of p16 (9p21), TMPRSS2-ERG or ETV1 Fusions (21q22; 7p21), chromosome 3, chromosome 7, chromosome 8, chromosome 10, and chromosome 17, alone or in further view of the number of hybridization complexes comprising one or more of p27Kip1 (4q43), CDK2 (12q13), cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homol (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12), the method further comprises determining the copy number of MYC (8p24), LPL (8p22), PTEN (10q23; see, e.g., U.S. Pat. Nos. 6,262,242; 6,482,795; and 7,217,795), and chromosome 8, alone or in further combination with the copy number of one or more of p16 (9p21), chromosome 3, chromosome 7, chromosome 10, and chromosome 17, as well as TMPRSS2-ERG or ETV1 Fusions (21q22; 7p21) and deletions and/or translocations thereof, alone or in further combination with the copy number of one or more of p27Kip1 (4q43), CDK2 (12q13), cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homol (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12). If desired, the copy number can be compared to a pre-determined cut-off, wherein a copy number greater than the pre-determined cut-off (i.e., for a gain) and a copy number less than the pre-determined cut-off (i.e., for a loss), as appropriate, indicates that the patient has prostate cancer. When about 20% or more of the examined prostate cells from a patient have translocations and/or deletions involving TMPRSS2-ERG or ETV1 Fusions (21q22; 7p21), the patient is considered to have prostate cancer.

While deparaffinization, pretreatment, staining, and routine slide washing also can be conducted in accordance with methods known in the art, use of an automated system, however, such as the VP 2000 Process (Abbott Molecular, Inc., Des Plaines, Ill.), decreases the amount of time needed to prepare slides for evaluation. Slides can be prepared in large batches (e.g., 50 slides), as opposed to small batches (e.g., 4 slides) when standard Coplin jars are used for post-hybridization washing. In addition, the scoring of slides can be fully automated using automated imaging, thereby reducing the amount of hands-on time required for specimen analysis. Full automation also enables the use of an imaging algorithm that captures more abnormal cells more frequently and consistently. Also, while any suitable method of slide preparation known in the art can be used, slides are preferably prepared using ThinPrep 2000 (Hologic, Inc., Bedford, Mass.), which generates more uniform and consistent monolayers of cells.

Other methods already known in the art or currently under development may require or prefer the use of a sample of prostate cells that is other than cells fixed in formalin and embedded in paraffin, e.g., fresh or frozen cells, homogenized cells, lysed cells, or isolated or purified nucleic acids (e.g., a "nucleic acid sample" such as DNA) from prostate cells ("sample of prostate cells" as used herein is intended to encompass all forms of a sample of prostate cells that enable the determination of copy number and gain/loss). Nuclei also can be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution, such as formaldehyde.

Examples of methods that can be used herein include, but are not limited to, quantitative polymerase chain reaction (Q-PCR), real-time Q-PCR (Applied Biosystems, Foster City, Calif.), densitometric scanning of PCR products, digital PCR, optionally with pre-amplification of the gene(s) and/or chromosomal region(s) for which copy number(s) is/are to be determined (see, e.g., Vogelstein et al., PNAS USA 96: 9236-9241 (1999); U.S. Pat. App. Pub. No. 2005/0252773; and U.S. Pat. App. Pub. No. 2009/0069194), comparative genomic hybridization (CGH; see, e.g., Kallioniemi et al., Science 258: 818-821 (1992); and Int'l Pat. App. Pub. No. WO 93/18186), microsatellite or Southern allelotype analysis, dot blots, arrays, microarrays (Carter, Nature Genetics Supplement 39: S16-S21 (July 2007)), multiplex amplifiable probe hybridization (MAPH), multiplex ligation-dependent probe amplification (MLPA; see, e.g., Schouten et al., Nucleic Acids Res. 30: e 57 (2002)), denaturing high performance liquid chromatography (dHPLC; Kumar et al., J. Biochem. Biophys. Methods 64(3): 226-234 (2005)), dynamic allele-specific hybridization (DASH), measuring fluorescent probe lengths on combed genomic DNA (Herrick et al., PNAS 97(1): 222-227 (2000)), reference query pyrosequencing (RQPS; Liu et al., Cold Spring Harb. Protoc. doi: 10.1101/pdb.prot5491 (2010)), mapping of fosmid ends onto a reference sequence (capillary-based technology), microelectrophoretic and nanopore sequencing (see, e.g., Service, Science 311: 1544-1546 (2006); and Shendure et al., Nat. Rev. Genet. 5: 335-344 (2004)), and the like.

Denaturation of nucleic acid targets for analysis by in situ hybridization and similar methods typically is done in such a manner as to preserve cell morphology. For example, chromosomal DNA can be denatured by high pH, heat (e.g., temperatures from about 70-95° C.), organic solvents (e.g., formamide), and combinations thereof. Probes, on the other hand, can be denatured by heat in a matter of minutes.

After denaturation, hybridization is carried out. Conditions for specifically hybridizing the probes to their nucleic acid targets generally include the combinations of conditions that are employable in a given hybridization procedure to produce specific hybrids, the conditions of which may easily be determined by one of ordinary skill in the art. Such conditions typically involve controlled temperature, liquid phase, and contact between a probe and a target. Hybridization conditions vary depending upon many factors including probe concentration, target length, target and probe G-C content, solvent composition, temperature, and duration of incubation. At least one denaturation step can precede contact of the probes with the targets. Alternatively, the probe and the target can be subjected to denaturing conditions together while in contact with one another, or with subsequent contact of the probe with the biological sample. Hybridization can be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, a blocking agent, such as unlabeled blocking nucleic acid, as described in U.S. Pat. No. 5,756,696 (the contents of which are herein incorporated by reference in their entirety, and specifically for the description of the use of blocking nucleic acid), can be used. Other conditions can be readily employed for specifically hybridizing the probes to their nucleic acid targets present in the sample, as would be readily apparent to one of skill in the art. Hybridization protocols are described, for example, in Pinket et al., PNAS USA 85: 9138-9142 (1988); In situ Hybridization Protocols, Methods in Molecular Biology, Vol. 33, Choo, ed., Humana Press, Totowa, N.J. (1994); and Kallioniemi et al., PNAS USA 89: 5321-5325 (1992).

Upon completion of a suitable incubation period, non-specific binding of chromosomal probes to sample DNA can be removed by a series of washes. Temperature and salt concentrations are suitably chosen for a desired stringency. The level of stringency required depends on the complexity of a specific probe sequence in relation to the genomic sequence, and can be determined by systematically hybridizing probes to samples of known genetic composition. In general, high stringency washes can be carried out at a temperature in the range of about 65 to about 80° C. with about 0.2× to about 2×SSC and about 0.1% to about 1% of a non-ionic detergent, such as Nonidet P-40 (NP40). If lower stringency washes are required, the washes can be carried out at a lower temperature with an increased concentration of salt.

When fluorophore-labeled probes or probe compositions are used, the detection method can involve fluorescence microscopy, flow cytometry, or other means for determining probe hybridization. Any suitable microscopic imaging method can be used in conjunction with the methods described herein for observing multiple fluorophores. In the case where fluorescence microscopy is employed, hybridized samples can be viewed under light suitable for excitation of each fluorophore and with the use of an appropriate filter or filters. Automated digital imaging systems, such as the MetaSystems, BioView or Applied Imaging systems, alternatively can be used, along with signal enumeration and data acquisition algorithms.

Depending on the method employed, a digital image analysis system can be used to facilitate the display of results and to improve the sensitivity of detecting small differences in fluorescence intensity. An exemplary system is QUIPS (an acronym for quantitative image processing system), which is an automated image analysis system based on a standard fluorescence microscope equipped with an automated stage, focus control and filter wheel (Ludl Electronic Products, Ltd., Hawthorne, N.Y.). The filter wheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display, which is used for finding interesting areas on a slide as well as for focusing. The other camera port has a cooled CCD camera (model 200 by Photometrics Ltd., Tucson, Ariz.), which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In array CGH (aCGH) the probes are immobilized at distinct locations on a substrate and are not labeled (see, e.g., Int'l Pat. App. Pub. No. WO 96/17958). Instead, sample nucleic acids, which comprise target nucleic acid(s), are labeled. Either the sample nucleic acids are labeled prior to hybridization or the hybridization complexes are detectably labeled. In dual- or multi-color aCGH the probe array is simultaneously or sequentially hybridized to two or more collections of differently labeled target nucleic acids.

Preferably, biomarker expression is assessed by immunofluorescence (IF) to locate areas for analysis by FISH. IF results closely correlate with FISH abnormalities identified using the probes described herein as well as morphological assessment of a tumor.

The above methods can be used to stratify patients into those who need repeat biopsy or intensive follow-up and those who do not. The above methods also can be used to distinguish prostate cancer from a benign condition, such as benign prostatic hyperplasia (BPH). Such methods can be used in conjunction with other methods, such as histological tissue evaluation, prostate-specific antigen (PSA) detection, nomogram (e.g., Katan nomogram), methylation, and mutation. In this regard, the methods also can be used to confirm diagnosis after radical prostatectomy and to distinguish prostate cancer from a pre-cancerous lesion (e.g., atypical small acinar proliferation in the prostate (ASAP), low-grade prostate intra-epithelial neoplasia (PIN), and high-grade PIN) in the prostate and a pre-cancerous lesion in the prostate from a benign condition, such as BPH. The methods can aid in the diagnosis of adenocarcinoma in a specimen obtained by biopsy, trans-urethral resection (TURP), or surgery, e.g., radical prostatectomy. An advantage of the above methods, particularly in the context of detection and diagnosis, is that chromosomal abnormalities indicative of prostate cancer can be detected in cells surrounding a tumor (i.e., "field effect" cells). Thus, even if the tumor is missed during biopsy, its presence can be detected in accordance with the above methods, thereby reducing false negative results and the need for repeat biopsies. The methods also can be used in the prognosis of prostate cancer, the monitoring of the efficacy of the prophylactic or therapeutic treatment (e.g., hormone or radiation therapy) of prostate cancer, and the monitoring of the recurrence of prostate cancer. The methods can be used to confirm results obtained with urine- or blood-based detection methods. The risk of cancer in patients with pre-cancerous lesions can be assessed using such methods, as well as the aggressiveness of the cancer (e.g., more chromosomal abnormalities and/or more widespread chromosomal abnormalities in the field effect cells). Such methods also can be used to aid in treatment decisions, e.g., active surveillance, surgery, or therapy with hormones or radiation, and adjuvant treatment decisions, such as in the context of radical prostatectomy.

Thus, the method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a sample of prostate cells for chromosomal abnormalities. Generally, in making such a comparison, the predetermined level is obtained by running a particular assay a sufficient number of times and under appropriate conditions such that a linkage or association of a particular chromosomal abnormality (presence or level) with a particular stage or endpoint of a disease, disorder or condition (e.g., preeclampsia or cardiovascular disease) or with particular indicia can be made. Typically, the predetermined level is obtained with assays of reference subjects (or populations of subjects).

In particular, with respect to a predetermined level as employed for monitoring disease progression and/or treatment, the chromosomal abnormality (presence or level) may be "unchanged," "favorable" (or "favorably altered"), or "unfavorable" (or "unfavorably altered"). "Elevated" or "increased" refers to a level of chromosomal abnormality in a sample of prostate cells that is higher than a typical or normal level or range (e.g., predetermined level), or is higher than another reference level or range (e.g., earlier or baseline sample). The term "lowered" or "reduced" refers to a level of chromosomal abnormality in a sample of prostate cells that is lower than a typical or normal level or range (e.g., predetermined level), or is lower than another reference level or range (e.g., earlier or baseline sample). The term "altered" refers to a level of chromosomal abnormality in a sample of prostate cells that is altered (increased or decreased) over a typical or normal level or range (e.g., predetermined level), or over another reference level or range (e.g., earlier or baseline sample).

The typical or normal level or range for a given chromosomal abnormality is defined in accordance with standard practice. Because the levels of chromosomal abnormalities in some instances will be very low, a so-called altered level or alteration can be considered to have occurred when there is any net change as compared to the typical or normal level or range, or reference level or range, which cannot be explained by experimental error or sample variation. Thus, the level measured in a particular sample will be compared with the level or range of levels determined in similar samples from a so-called normal subject. In this context, a "normal subject" is an individual with no detectable disease, and a "normal" or "control" patient or population is/are one(s) that exhibit(s) no detectable disease, respectively, for example. Furthermore, given that chromosomal abnormalities are not routinely found at high levels in the majority of the human population, a "normal subject" can be considered an individual with no substantial detectable increased level of a given chromosomal abnormality, and a "normal" (sometimes termed "control") patient or population is/are one(s) that exhibit(s) no substantial detectable increased level of a given chromosomal abnormality. An "apparently normal subject" is one in which chromosomal abnormalities have not been or are being assessed. The level of a given chromosomal abnormality is said to be "elevated" when the chromosomal abnormality is normally undetectable, but is detected in a test sample, as well as when the analyte is present in the test sample at a higher than normal level. Thus, inter alia, the disclosure provides a method of screening for a subject having, or at risk of having, prostate cancer.

The method can also involve the detection of other markers and the like. For example, the method can also involve the detection of prostate-specific antigen (PSA), for example.

The methods described herein also can be used to determine whether or not a subject has or is at risk of developing prostate cancer. Specifically, such a method can comprise the steps of:

(a) determining chromosomal abnormalities in a sample of prostate cells from a subject (e.g., using the methods described herein, or methods known in the art); and (b) comparing the levels of chromosomal abnormalities determined in step (a) with predetermined levels, wherein, if the levels of chromosomal abnormalities determined in step (a) are favorable with respect to predetermined levels, then the subject is determined not to have or be at risk for prostate cancer. However, if the levels of chromosomal abnormalities determined in step (a) are unfavorable with respect to predetermined levels, then the subject is determined to have or be at risk for prostate cancer.

Additionally, provided herein is method of monitoring the progression of prostate cancer in a subject. Optimally, the method comprises the steps of:

(a) determining chromosomal abnormalities in a sample of prostate cells from a subject;

(b) determining the levels of chromosomal abnormalities in a later sample of prostate cells from the subject; and (c) comparing the levels of chromosomal abnormalities as determined in step (b) with the levels of chromosomal abnormalities as determined in step (a), wherein if the levels in step (b) are unchanged or unfavorable when compared to the levels determined in step (a), then prostate cancer is determined to have continued, progressed or worsened in the subject. By comparison, if the levels as determined in step (b) are favorable when compared to the levels as determined in step (a), then prostate cancer is determined to have discontinued, regressed or improved in the subject.

Optionally, the method further comprises comparing the levels of chromosomal abnormalities as determined in step (b), for example, with predetermined levels. Further, optionally the method comprises treating the subject, e.g., with one or more pharmaceutical compositions, radiation, and/or hormone therapy, for a period of time if the comparison shows that the levels as determined in step (b), for example, are unfavorably altered with respect to the predetermined levels.

Still further, the methods can be used to monitor treatment in a subject receiving treatment, e.g., with one or more pharmaceutical compositions, radiation, and/or hormone therapy. Specifically, such methods involve providing a first sample of prostate cells from a subject before the subject has been treated. Next, the levels of chromosomal abnormalities in the first sample of prostate cells are determined (e.g., using the methods described herein or as known in the art). After the levels of chromosomal abnormalities are determined, optionally the levels are then compared with predetermined levels. If the levels as determined in the first sample of prostate cells are lower than the predetermined levels, then the subject is not treated. However, if the levels as determined in the first sample of prostate cells are higher than the predetermined levels, then the subject is treated for a period of time. The period of time that the subject is treated can be determined by one skilled in the art (for example, the period of time can be from about seven (7) days to about two years, preferably from about fourteen (14) days to about one (1) year).

During the course of treatment, second and subsequent samples of prostate cells are then obtained from the subject. The number of samples and the time in which said samples are obtained from the subject are not critical. For example, a second sample could be obtained seven (7) days after the subject is first treated, a third sample could be obtained two (2) weeks after the subject is first treated, a fourth sample could be obtained three (3) weeks after the subject is first treated, a fifth sample could be obtained four (4) weeks after the subject is first treated, etc.

After each second or subsequent sample is obtained from the subject, the levels of chromosomal abnormalities in the second or subsequent sample are determined (e.g., using the methods described herein or as known in the art). The levels as determined in each of the second and subsequent samples are then compared with the levels as determined in the first sample (e.g., the sample that was originally optionally compared to the predetermined level). If the levels as determined in step (c) are favorable when compared to the levels as determined in step (a), then prostate cancer is determined to have discontinued, regressed or improved, and the subject should continue to be treated. However, if the levels determined in step (c) are unchanged or unfavorable when compared to the levels as determined in step (a), then prostate cancer is determined to have continued, progressed or worsened, and the subject should be treated with a higher dosage of pharmaceutical composition, radiation, or hormone, for example, or the subject should be treated differently.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained.

Moreover, the present disclosure also relates to methods of determining whether a subject predisposed to or suffering from prostate cancer will benefit from treatment. In particular, the disclosure relates to companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, prostate cancer is a candidate for therapy. Generally, the subject is one who has experienced some symptom of the disease or who has actually been diagnosed as having, or being at risk for, such a disease, and/or who demonstrates unfavorable levels of chromosomal abnormalities, as described herein.

The method optionally comprises an assay as described herein, where levels of chromosomal abnormalities are assessed before and following treatment of a subject. The observation of unfavorable levels of chromosomal abnormalities following treatment confirms that the subject will not benefit from receiving further or continued treatment, whereas the observation of favorable levels of chromosomal abnormalities following treatment confirms that the subject will benefit from receiving further or continued treatment. This confirmation assists with management of clinical studies, and provision of improved patient care.

Probes

A set of probes is also provided. In one embodiment, the set of probes comprises a locus-specific probe for MYC (8q24), a locus-specific probe for phosphatase and tensin homolog (PTEN; 10q23), a centromeric probe for chromosome 8, and a centromeric probe for chromosome 7, wherein the set of probes optionally further comprises an anti-α-methylacyl-CoA racemase (AMACR) antibody, which can be detectably labeled. In another embodiment, the set of probes comprising a locus-specific probe for MYC (8q24), a locus-specific probe for lipoprotein lipase (LPL; 8p22), a locus-specific probe for PTEN, and a centromeric probe for chromosome 8. The set of probes optionally further comprises an anti-AMACR antibody, which can be detectably labeled. The locus-specific probe for MYC (8q24) preferably covers approximately 820 kb, such as 821 kb, centered on the MYC gene and includes the whole MYC gene as well as adjacent regions (see discussion of "MYC" in method section above). The locus-specific probe for LPL (8p22) preferably covers approximately 170 kb centered on the LPL gene and includes the whole LPL gene as well as adjacent regions (see discussion of "LPL" in method section above). The locus-specific probe for PTEN (10q23) preferably covers approximately 365 to 370 kb, such as 368 kb, centered on the PTEN gene and includes the whole PTEN gene as well as adjacent regions, such as STS markers D10S215 on the centromeric side and RH93626 on the telomeric side (see discussion of "PTEN" in method section above). The set of probes can optionally further comprise one or more of a locus-specific probe for p16 (9p21), TMPRSS2-ERG or ETV1 fusions (21q22; 7p21 locus), a centromeric probe for chromosome 3, a centromeric probe for chromosome 7, a centromeric probe for chromosome 10, and a centromeric probe for chromosome 17. The set of probes can further comprise one or more of a locus-specific probe for cyclin-dependent kinase inhibitor p27Kip1 (4q43), a locus-specific probe for CDK2; 12q13), a locus-specific probe for cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homolog (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12).

Suitable probes for use as locus-specific probes hybridize to a specific region on a chromosome containing a gene. The locus-specific probe for the gene MYC (8p24) can hybridize to all or a portion of the MYC gene at p24 on chromosome 8 (i.e., 8p24). The locus-specific probe for the gene LPL (8p22) can hybridize to all or a portion of the LPL gene at p22 on chromosome 8 (i.e., 8p22). The locus-specific probe for the gene PTEN (10q23) can hybridize to all or a portion of the PTEN gene at q23 on chromosome 10 (i.e., 10q23). Similarly, the locus-specific probe for p27Kip1 (4q43) can hybridize to all or a portion of the p27Kip1 gene at q43 on chromosome 4 (i.e., 4q43), the locus-specific probe for CDK2 (12q13) can hybridize to all or a portion of the CDK2 gene at q13 on chromosome 12 (i.e., 12q13), the locus-specific probe for cyclin E (CCNE1; 19q12 and CCNE2; 8q22) can hybridize to all or a portion of the CCNE1 gene at q12 on chromosome 19 or all or a portion of the CCNE2 gene at q22 on chromosome 8, a locus-specific probe for retinoblastoma 1 (Rb1; 13q14) can hybridize to all or a portion of the Rb1 gene at q14 on chromosome 13, a locus-specific probe for NK3 homeobox 1 (NKX3.1; 8p21.2) can hybridize to all or a portion of the NKX3.1 gene at p21.2 on chromosome 8, a locus-specific probe for epidermal growth factor receptor (EGFR; 7p11) can hybridize to all or a portion of the EGFR gene at p11 on chromosome 7, a locus-specific probe for phosphoinositide-3-kinase (PI3K; 3q26) can hybridize to all or a portion of the PI3K gene at q26 on chromosome 3, a locus-specific probe for AKT1 kinase (Akt1; 14q32) can hybridize to all or a portion of the Akt1 gene at q32 on chromosome 14, a locus-specific probe for FKHR (FOXO1; 13q14.11) can hybridize to all or a portion of the FOXO1 gene at q14.11 on chromosome 13, a locus-specific probe for p53 binding protein homolog (MDM2; 12q14.3-12q15) can hybridize to all or a portion of the MDM2 gene at q14.3-q15 on chromosome 12, a locus-specific probe for p53 (17p13.1) can hybridize to all or a portion of the p53 gene at p13.1 on chromosome 17, a locus-specific probe for v-Ki-ras2 Kirsten rat sarcoma viral oncogene homolog (KRAS; 12p12.1) can hybridize to all or a portion of the KRAS gene at p12.1 on chromosome 12, a locus-specific probe for v-raf murine sarcoma viral oncogene homolog B1 (BRAF; 7q34) can hybridize to all or a portion of the BRAF gene at q34 on chromosome 7, a locus-specific probe for cyclin D1 (CCND1; 11q13) can hybridize to all or a portion of the CCND1 gene at q13 on chromosome 11, a locus-specific probe for B-cell CLL/lymphoma 2 (BCL2; 18q21.3/18q21.33) can hybridize to all or a portion of the BCL2 gene at q21.3-q21.33 on chromosome 18, and a locus-specific probe for androgen receptor (AR; Xq12) can hybridize to all or a portion of the AR gene at q12 on chromosome X.

A suitable probe for use as a break-away probe hybridizes to TMPRSS2 (21q22), thereby enabling the detection of translocations and/or deletions.

Suitable probes for use as chromosomal probes hybridize with repetitive DNA associated with the centromere of a chromosome. Centromeres of primate chromosomes contain a complex family of long-tandem repeats of DNA, which are composed of a monomer repeat length of about 171 base pairs (bp), that is referred to as α-satellite DNA. Chromosomal probes are typically about 50-1×10$^5$ nucleotides in length. Longer probes typically are fragmented to about 100-600 nucleotides in length. The probe for chromosome 3 can hybridize to the alpha satellite DNA located at the centromere of chromosome 3, whereas the probe for chromosome 7 can hybridize to alpha satellite DNA located at the centromere of chromosome 7, the probe for chromosome 8 can hybridize to alpha satellite DNA located at the centromere of chromosome 8, the probe for chromosome 10 can hybridize to alpha satellite DNA located at the centromere of chromosome 10, and the probe for chromosome 17 can hybridize to the alpha satellite DNA located at the centromere of chromosome 17. Examples of such probes include CEP3, CEP7, CEP8, CEP 10 and CEP17.

Chromosome enumerator probes (CEP) and locus-specific probes that target a chromosome region or subregion can be obtained commercially or readily prepared by those in the art. Such probes can be commercially obtained from Abbott Molecular, Inc. (Des Plaines, Ill.), Molecular Probes, Inc. (Eugene, Oreg.), or Cytocell (Oxfordshire, UK). Chromosomal probes can be prepared, for example, from protein nucleic acids (PNA), cloned human DNA such as plasmids, bacterial artificial chromosomes (BACs), and P1 artificial chromosomes (PACs) that contain inserts of human DNA sequences. A region of interest can be obtained via PCR amplification or cloning. In another embodiment, the chromosomal probes can be oligo probes. Alternatively, chromosomal probes can be prepared synthetically in accordance with methods known in the art.

When targeting of a particular gene locus is desired, probes that hybridize along the entire length of the targeted gene can be preferred, although not required. A locus-specific probe can be designed to hybridize to an oncogene or tumor suppressor gene, the genetic aberration of which is correlated with metastasis, e.g., MYC.

The probes can be prepared by any method known in the art. Probes can be synthesized or recombinantly produced. Such probes can range in length from about 25,000 base pairs to about 800,000 base pairs.

Preferably, probes are detectably labeled, and each probe is distinctly labeled. Preferably, the probes are detectably labeled with fluorophores, and each probe is distinctly labeled. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethy-4-bora-3a,4a-diaza-3-indacenepropionic acid, eosin-5-isothiocyanate, erythrosine-5-isothiocyanate, SpectrumRed (Abbott Molecular, Inc.), SpectrumGold (Abbott Molecular, Inc.), SpectrumGreen (Abbott Molecular, Inc.), SpectrumAqua (Abbott Molecular, Inc.), TEXAS RED (Molecular Probes, Inc.), Lucifer yellow, and CASCADE blue acetylazide (Molecular Probes, Inc.). The particular label used is not critical; desirably, however, the particular label does not interfere with in situ hybridization of the probe and the detection of label on any other probe. The label desirably is detectable in as low copy number as possible to maximize the sensitivity of the assay and be detectable above any background signal. Also desirably, the label provides a highly localized signal, thereby providing a high degree of spatial resolution.

Attachment of fluorophores to nucleic acid probes is well-known in the art and can be accomplished by any available means. Fluorophores can be covalently attached to a particular nucleotide, for example, and the labeled nucleotide incorporated into the probe using standard techniques such as nick translation, random priming (Rigby et al., J. Mol. Biol. 113: 237 (1997)), PCR labeling, end labeling, direct labeling by chemical modification of particular residues, such as cytosine residues (U.S. Pat. No. 5,491,224), and the like. Alternatively, the fluorophore can be covalently attached to nucleotides with activated linker arms, which have been incorporated into the probe, for example, via a linker to the deoxycytidine nucleotides of the probe that have been transaminated. Methods for labeling probes are described in U.S. Pat. No. 5,491,224, and Morrison et al., Molecular Cytogenetics: Protocols and Applications, Chapter 2, "Labeling Fluorescence In Situ Hybridization Probes for Genomic Targets," pp. 21-40, Fan, Ed., Humana Press (2002), both of which are herein incorporated by reference for their descriptions of labeling probes.

One of skill in the art will recognize that other agents or dyes can be used in lieu of fluorophores as label-containing moieties. Luminescent agents include, for example, radioluminescent, chemiluminescent, bioluminescent, and phosphorescent label-containing moieties. Agents that are detectable with visible light include cyanin dyes. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes can be achieved as described below.

Chromosomal probes hybridized to target regions alternatively can be visualized by enzymatic reactions of label moieties with suitable substrates for the production of insoluble color products. Each probe can be discriminated from other probes within the set by choice of a distinct label moiety. A biotin-containing probe within a set can be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzoate serves as a substrate for HRP.

Kit

Also provided is a kit. In one embodiment, the kit comprises (a) a set of probes that enables diagnosis of prostate cancer in a patient, wherein the set of probes comprises a locus-specific probe for MYC, a locus-specific probe for phosphatase and tensin homolog (PTEN), a centromeric probe for chromosome 8, and a centromeric probe for chromosome 7, and (b) instructions for diagnosing prostate cancer in a patient, wherein the instructions comprise determining in a sample of prostate cells obtained from the patient the presence of chromosomal abnormalities. A MYC % gain (% gain is % of cells with MYC>2 signals) of greater than 35 (with a range of 2 to 50), a PTEN % loss (% loss is % of cells with <2 signals) of greater than 33 (with a range of 29 to 33), a chromosome 8% gain (% gain is % of cells with >2 signals) of greater than 34 (with a range of 32 to 34), and a chromosome 7% abnormal (% abnormal is % of cells with >2 or <2 signals) greater than 28 (with a range of 24 to 29) in a sample of prostate cells from a tumor region of interest (ROI) or a benign ROI of the prostate of the patient indicates that the patient has prostate cancer. In another embodiment, the kit comprises (a) a set of probes that enables diagnosis of prostate cancer in a patient and (b) instructions for detecting, diagnosing, prognosticating, or assessing the therapeutic/prophylactic treatment of prostate cancer in a patient. Thus, the kit can comprise (a) a set of probes that enables diagnosis of prostate cancer in a patient, wherein the set of probes comprises a locus-specific probe for MYC, a locus-specific probe for lipoprotein lipase (LPL), a locus-specific probe for PTEN, and a centromeric probe for chromosome 8 and (b) instructions for diagnosing prostate cancer in a patient, wherein the instructions comprise determining in a sample of prostate cells obtained from the patient the presence of chromosomal abnormalities. A MYC/LPL % gain (% gain is % of cells with MYC/LPL>1) of greater than 14 (with a range of 12 to 22), a chromosome 8% abnormal (% abnormal is % of cells with >2 or <2 signals) of greater than 34 (with a range of 26 to 40), a PTEN % loss (% loss is % of cells with <2 signals) of greater than 44 (with a range of 22 to 54), or a MYC/chromosome 8% gain (% gain is % of cells with MYC/chromosome 8>1) greater than 16 (with a range of 10 to 18) in a sample of prostate cells from a tumor ROI of the prostate of the patient indicates that the patient has prostate cancer. A MYC/LPL % gain of greater than 18 (with a range of 12 to 19), a chromosome 8% abnormal of greater than 32 (with a range of 25 to 34), a PTEN % loss of greater than 26 (with a range of 22 to 28), or a MYC/chromosome 8% gain greater than 16 (with a range of 9 to 18) in a sample of prostate cells from a benign ROI of the prostate of the patient indicates that the patient has prostate cancer. The set of probes can further comprise one or more of a locus-specific probe for p16 (9p21), TMPRSS2-ERG or ETV1 fusions (21q22; 7p21 locus), a centromeric probe for chromosome 3, a centromeric probe for chromosome 7, a centromeric probe for chromosome 10, and a centromeric probe for chromosome 17. The set of probes can further comprise one or more of a locus-specific probe for cyclin-dependent kinase inhibitor p27Kip1 (4q43), a locus-specific probe for CDK2; 12q13), a locus-specific probe for cyclin E (CCNE1; 19q12 and CCNE2; 8q22), a locus-specific probe for retinoblastoma 1 (Rb1; 13q14), a locus-specific probe for NK3 homeobox 1 (NKX3.1; 8p21.2), a locus-specific probe for epidermal growth factor receptor (EGFR; 7p11), a locus-specific probe for phosphoinositide-3-kinase (PI3K; 3q26), a locus-specific probe for AKT1 kinase (Akt1; 14q32), a locus-specific probe for FKHR (FOXO1; 13q14.11), a locus-specific probe for p53 binding protein homolog (MDM2; 12q14.3-12q15), a locus-specific probe for p53 (17p13.1), a locus-specific probe for v-Ki-ras2 Kirsten rat sarcoma viral oncogene homolog (KRAS; 12p12.1), a locus-specific probe for v-raf murine sarcoma viral oncogene homolog B1 (BRAF; 7q34), a locus-specific probe for cyclin D1 (CCND1; 11q13), a locus-specific probe for B-cell CLL/lymphoma 2 (BCL2; 18q21.3/18q21.33), and a locus-specific probe for androgen receptor (AR; Xq12). The kit can further comprise instructions for morphologically assessing a section of a prostate from a patient and identifying at least one tumor ROI, at least one benign ROI, or at least one tumor ROI and at least one benign ROI prior to determining the presence of chromosomal abnormalities.

Alternatively, the kit can further comprise instructions for assessing a section of a prostate from a patient by immunofluorescence and identifying the presence of a tumor ROI prior to determining the presence of chromosomal abnormalities, in which case the kit can further comprise an anti-α-methylacyl-CoA racemase (AMACR) antibody, which can be detectably labeled, and the instructions for assessing a section of a prostate from a patient by immunofluorescence can further comprise contacting the section with detectably labeled anti-AMACR antibody and detecting over-expression of AMACR, wherein over-expression of AMACR in a region of the section indicates the presence of a tumor ROI. The instructions can further comprise treating the section with heat-induced epitope retrieval prior to assessing the section of a prostate from a patient by immunofluorescence. Such kits may further comprise blocking agents or other probes, various labels or labeling agents to facilitate detection of the probes, reagents for hybridization (e.g., buffers), a metaphase spread, and the like.

EXAMPLES

The following examples serve to illustrate the present invention. The examples are not intended to limit the scope of the claimed invention in any way.

Example 1

This example describes the analysis of prostate specimens using various combinations of probes and fluorescent in situ hybridization (FISH).

Radical prostatectomy specimens from 16 patients with adenocarcinoma of the prostate were collected at Rush Medical Center, Chicago, Ill. Two sets of formalin-fixed, paraffin-embedded (FFPE) slides were available from nine patients: one set containing the tumor area scribed by a pathologist (tumor region of interest (ROI)) and the other set containing an area distant from the tumor (distant ROI). Slides from 11 patients with benign prostatic hyperplasia (BPH) were collected by trans-urethral resection of the prostate (TURP) and used as controls.

The slides were pre-treated by incubation in 1×SSC (15 mM citric acid and 0.15 M NaCl) and subsequent pepsin digestion. The slides were hybridized by multi-color FISH with the following probe sets: MYC, LPL, and chromosome enumerator probe (CEP) 8; PTEN, CEP10®, and CEP7®; TMPRSS2-ERG or ETV1 fusions; and CEP8®, CEP7®, CEP17®, and p16. Several fields were evaluated. Twenty five to 50 cells/specimen were enumerated for the number of fluorescent signals for each probe in the set. All patterns of re-arrangement and copy number changes were observed and recorded for the TMPRSS2 break-away probe. Slides from distant ROI were scanned for most abnormal FISH signal patterns, and the fields of view containing these patterns and the adjacent regions were enumerated.

Tumor ROI in specimens from radical prostatectomy bore chromosomal abnormalities, including MYC amplification/gain, LPL loss, PTEN loss, TMPRSS2 rearrangement, and aneusomy. Significant chromosomal abnormalities were also observed in benign slides containing distant ROI. Enumeration results were analyzed to determine a cut-off for each individual probe or for a derivative classifier, such as a ratio of two probes, which would best discriminate patterns of abnormalities associated with cancer from patterns in apparently benign tissue in the BPH specimens. The cut-off was based on percentage of cells containing a genomic abnormality. A fixed cut-off of a signal count less than the benign mean signal count minus 3 standard deviations was used to establish a loss, whereas a fixed cut-off of a signal count greater than the benign mean signal count plus three standard deviations was used to establish a gain. The cut-off for TMPRSS2 rearrangement was greater than about 20% of the cells within the evaluated region containing the rearrangement. Based on the fixed cut-offs, a gain of MYC and aneusomy were found in 15/16 tumor ROI and TMPRSS2 rearrangement was found in 11/16 tumor ROI, whereas a gain of MYC and aneusomy were found in 2/9 distant ROI and TMPRSS2 rearrangement was found in 5/9 distant ROI. The results of the analysis further demonstrated that the detection of several chromosomal abnormalities at the selected cut-offs was highly specific to specimens from adenocarcinoma patients.

Example 2

This example describes the analysis of prostate specimens with FISH using various combinations of probes.

A total of six probes were used for evaluation. These six probes consisted of three centromeric probes (CEP®) for chromosomes 7, 8, and 10, as well as three locus-specific identifier (LSI®) probes (MYC (8q24), LPL (8p21-22), and PTEN (10q23)). Selection of probes was based on literature review that revealed frequent aberrations in prostate cancer (Bova et al., Cancer Res. 53: 3869-3873 (1993); Kagan et al., Oncogene 11: 2121-2126 (1995); Emmert-Buck et al., Cancer Res. 55: 2959-2962 (1995); Yoshimoto et al. (2007), supra; and Kazunari et al., J. Nat'l Cancer Inst. 9(18): 1574-1580 (1999)). LSI® and CEP® probes were obtained from Vysis/Abbott Molecular, Inc. (Des Plaines, Ill.). The probes included for subsequent evaluation were combined into two probe sets. The first probe set was ProVysion®, which consisted of MYC 8q24 (SpectrumGreen™), LPL 8p21-22 (SpectrumOrange™), and CEP8® (SpectrumAqua™). The second probe set (PTEN set) included PTEN (SpectrumOrange™), CEP7® (Spectrum Aqua), and CEP10® (SpectrumGreen).

Thirty-three radical prostatectomy (RP) specimens from patients with adenocarcinoma of the prostate were obtained from Rush University Medical Center, Chicago, Ill. For each specimen, a tissue section of 4-6 µm was scribed by a pathologist to mark the tumor region(s). For 17 of the 33 RP cases, a second section was available with only histologically benign tissue. Twenty-six benign prostatic hyperplasia (BPH) specimens served as controls (Nakayama et al., J. Cell Biochem. 91(3): 540-552 (2004)). FISH signals for each of the 6 probes were enumerated in 50-100 cells per section.

For each specimen, a tissue section of 5 µm was scribed by a pathologist to mark tumor region(s), if present. FFPE tissue section slides were baked at 56° C. for 2-24 hours, pretreated three times in Hemo-De (Scientific Safety Solvents) for 5 minutes each at room temperature, rinsed twice in 100% ethanol for one minute each at room temperature, incubated in 45% formic acid/0.3% hydrogen peroxide for 15 minutes at room temperature, and then rinsed in deionized water for three minutes. Slides were then incubated in pre-treatment solution (1×SSC, pH 6.3) at 80° C. for 35 minutes, rinsed for three minutes in deionized water, incubated for 22 minutes in 0.15% pepsin in 0.1N HCl solution at 37° C., and rinsed again for three minutes in deionized water. Slides were dehydrated for 1 minute each in 70%, 85%, and 100% ethanol and then air dried. Ten microliters of each respective probe hybridization mix (LSI® buffer, blocking DNA, and labeled probes) were added to the specimens, and a coverslip was applied and sealed with rubber cement. Slides were codenatured for five minutes at 73° C. and hybridized for 16-24 hours at 37° C. on a ThermoBrite (Vysis/Abbott Molecular, Inc.). Following hybridization, coverslips were removed, and slides were washed in 2×SSC/0.3% NP-40 at 73° C. for two minutes and subsequently in 2×SSC/0.1% NP-40 for one minute at room temperature. Ten microliters of DAPI I counterstain were placed on the slide, and a coverslip was applied.

Following hybridization, FISH signal enumeration was performed. Each specimen was analyzed under a fluorescence microscope using single bandpass filters (Abbott Molecular, Des Plaines, Ill.) specific for DAPI (4,6-diamidino-2-phenylindole), SpectrumOrange™, SpectrumGreen™, and SpectrumAqua™. The number of FISH signals for each probe was recorded in a minimum of 50 consecutive nonoverlapped, intact interphase nuclei (such as nuclei of about 50-100 cells) in areas of interest, which were identified by DAPI staining of nuclei with reference to the corresponding H&E-stained tissue. The abnormality parameters taken into account for each probe were as follows: Gain: [Signal Count]>2, Loss: [Signal Count]<2, and Abnormal: [Signal Count]>2 or <2. Fixed cut-offs were calculated as "mean of % abnormal cell counts in 26 BPH specimens+3 S.D." Specimen abnormality was defined as "% abnormal cells≥cut-off."

Abnormal FISH signals were observed on the slides for MYC, LPL, CEP8®, PTEN, CEP10® and CEP7®. Chromosomal abnormalities for MYC amplification/gain, LPL and PTEN loss, and aneusomy were not only observed in tumor regions of interest (ROIs) of specimens from radical prostatectomy, but also some of the benign ROIs. Table 1 shows the summary of the enumeration data. Twenty-two out of 33 specimens had abnormalities that were detected with the ProVysion® probe set (66.7%), and 20 out of 33 specimens had abnormalities that were detected with the PTEN probe set (60.6%). The total abnormality detected for tumor ROI with ProVysion®+PTEN probe set was 23/33, which is 69.7%. More importantly, a significant number of chromosomal abnormalities was observed in 8 out of 17 slides (8/17=47.1%; 4/17=23.5% for ProVysion®; 6/17=35.3% PTEN probe set) containing ROI distant ("distant ROI") from a tumor (Table 1). Gain and loss of Chromosome 8 were observed simultaneously in one specimen among most of the prostate cancer cases analyzed.

TABLE 1

Chromosomal abnormalities from FISH enumeration data

| Specimen Number | Tumor ROI (33) | | Distant ROI (17 of 33) | |
|---|---|---|---|---|
| | ProVysion ® | PTEN set | ProVysion ® | PTEN set |
| 01 | POS | POS | POS | POS |
| 02 | NEG | NEG | NEG | NEG |
| 03 | POS | POS | NA | |
| 04 | NEG | NEG | NA | |
| 05 | POS | POS | NEG | NEG |
| 06 | NEG | NEG | NA | |
| 07 | NEG | NEG | NEG | NEG |
| 08 | NEG | NEG | NA | |
| 09 | POS | NEG | NA | |
| 10 | POS | POS | NA | |
| 11 | NEG | NEG | NEG | NEG |
| 12 | NEG | NEG | NEG | NEG |
| 13 | POS | POS | NEG | NEG |
| 14 | POS | NEG | NEG | NEG |
| 15 | NEG | NEG | NEG | NEG |
| 16 | NEG | NEG | NA | |
| 17 | POS | POS | NA | |
| 18 | POS | POS | POS | NEG |
| 19 | POS | POS | NA | |
| 20 | NEG | NEG | POS | NEG |
| 21 | NEG | POS | NA | |
| 22 | POS | POS | NEG | NEG |
| 23 | POS | POS | NA | |
| 24 | POS | NEG | NA | |
| 25 | POS | POS | NEG | POS |
| 26 | POS | POS | NA | |
| 27 | POS | POS | NEG | POS |
| 28 | POS | POS | NA | |
| 29 | POS | POS | NEG | POS |
| 30 | POS | POS | NA | |
| 31 | POS | POS | NA | |
| 32 | POS | POS | POS | POS |
| 33 | POS | POS | NEG | POS |

POS = positive
NEG = negative

Enumeration results were further analyzed by Receiver Operating Characteristic (ROC curve) using SAS version 8.2 (SCA #S05020002). To select probes and determine an optimal FISH analysis algorithm yielding the highest sensitivity and specificity, the following parameters were considered for each probe:
  % Gain, percent cells with >2 signals,
  % Loss, percent cells with <2 signals,
  % Abnormal, percent cells with >2 or <2 signals, and
  For 2 probe ratios (probe A/probe B), % Gain was percent of cells with A/B ratio>1, % Loss was percent of cells with A/B ratio<1.
A combination of MYC/LPL % Gain, PTEN % Loss, MYC/CEP80% Gain and CEP8® % abnormal parameters within the scribed tumor regions identified adenocarcinoma in 97.1% (33/34) of RP specimens, with a specificity of 96.2% (25/26) relative to BPH ($\chi2$ p<0.001). When detected in regions of normal histology, these abnormalities correlated with adenocarcinoma in 82.4% (14/17 RP specimens, $\chi2$ p<0.001 relative to BPH). Table 2 is the ROC Analysis Summary of AUC (Area Under the Curve), best specificity and sensitivity for each probe and probe combination.

TABLE 2

ROC Analysis

| | Tumor ROI | | | Benign ROI | | |
|---|---|---|---|---|---|---|
| Probes and Abnormalities | AUC | Spec | Sens | AUC | Spec | Sens |
| MYC/LPL % Gain OR CEP8 % Abnorm OR PTEN % Loss OR MYC/CEP8 % Gain | 0.98 | 96.2 | 97.1 | 0.85 | 82.4 | 80.8 |
| CEP7/CEP10 %ain | 0.68 | 69.2 | 58.8 | 0.62 | 84.6 | 47.1 |
| MYC/CEP8 % Gain | 0.91 | 88.5 | 76.5 | 0.48 | 61.5 | 70.6 |
| LPL/CEP8 % Loss | 0.85 | 84.6 | 82.4 | 0.60 | 84.6 | 47.1 |
| PTEN/CEP10 % Loss * + | 0.881 | 80.8 | 82.4 | 0.788 | 80.8 | 64.7 |
| MYC/LPL % Gain | 0.90 | 96.2 | 79.4 | 0.69 | 80.8 | 58.8 |
| CEP7 % Abnorm * + | 0.896 | 80.8 | 88.2 | 0.845 | 80.8 | 76.5 |
| CEP8 % Abnorm + | 0.966 | 88.5 | 94.1 | 0.752 | 76.9 | 64.7 |
| CEP10 % Abnorm + | 0.865 | 80.8 | 79.4 | 0.775 | 73.1 | 76.5 |
| MYC % Gain * + | 0.908 | 76.9 | 91.2 | 0.846 | 76.9 | 82.4 |
| LPL % Abnorm + | 0.945 | 92.3 | 79.4 | 0.736 | 76.9 | 64.7 |
| PTEN % Loss * + | 0.726 | 80.8 | 58.8 | 0.827 | 80.8 | 70.6 |
| CEP7 % Gain + | 0.886 | 84.6 | 85.3 | 0.77 | 76.9 | 70.6 |
| CEP8 % Gain * + | 0.853 | 76.9 | 79.4 | 0.871 | 76.9 | 82.4 |
| CEP10 % Gain + | 0.93 | 84.6 | 94.1 | 0.786 | 84.6 | 76.5 |

AUC = area under the curve
Spec = specificity
Sen s= sensitivity

We also used another method to analyze the data set that is first to screen for potential important FISH probes by comparing different specimen groups (tumor ROI vs. BPH, and benign ROI vs. BPH) using two-sample t-test. FISH parameters with significant p-values (p-value<0.05) from t-test were selected for further examination.

Sixteen parameters derived from genomic copy number detected by FISH were evaluated. These parameters were CEP10% Abnormal, CEP10% Gain, CEP7% Abnormal, CEP7% Gain, CEP8% Abnormal, CEP8% Gain, CEP8% Loss, MYC % Gain, LPL % Abnormal, LPL % Loss, PTEN % Loss, PTEN/CEP10% Loss, CEP7/CEP10% Gain, LPL/CEP8% Loss, MYC/CEP8% Gain and MYC/LPL% Gain. Results from t-test analyses demonstrated that for all of the 16 FISH parameters, their mean values were statistically different between tumor and BPH groups (Table 3).

TABLE 3 t-Test Comparing Tumor and BPH

| FISH Parameters | Tumor Mean(Std) | BPH Mean(Std) | p-value |
|---|---|---|---|
| CEP10 % Abnorm | 40.03(16.9) | 22.92(8.14) | <.0001 |
| CEP10 % Gain | 17.21(20.49) | 2.31(4.72) | 0.0002 |
| CEP7 % Abnorm | 37.83(16.99) | 19.46(6.44) | <.0001 |
| CEP7 % Gain | 15.87(22.22) | 1.54(3.93) | 0.0008 |
| CEP8 % Abnorm | 47.55(16.02) | 23(6.02) | <.0001 |
| CEP8 % Gain | 19.97(23.73) | 1.54(2.42) | <.0001 |
| CEP8 % Loss | 27.58(15.33) | 21.46(5.78) | 0.0383 |
| MYC % Gain | 25.61(29.13) | 1.85(2.71) | <.0001 |
| LPL % Abnorm | 57.45(22.86) | 22.69(8.58) | <.0001 |
| LPL % Loss | 46.95(25.91) | 21.62(8.69) | <.0001 |
| PTEN % Loss | 35.38(23.37) | 20.92(8.6) | 0.0018 |
| PTEN/CEP10 % Loss | 25.54(21.41) | 7.85(4.86) | <.0001 |
| CEP7/CEP10 % Gain | 19.72(13.49) | 12.15(5.36) | 0.0047 |
| LPL/CEP8 % Loss | 35.89(28.69) | 8.08(4.18) | <.0001 |

TABLE 3-continued t-Test Comparing Tumor and BPH

| FISH Parameters | Tumor Mean(Std) | BPH Mean(Std) | p-value |
|---|---|---|---|
| MYC/CEP8 % Gain | 26.12(20.53) | 7.77(4.25) | <.0001 |
| MYC/LPL % Gain | 37.52(26.36) | 8.08(4.75) | <.0001 |

Results from t-test of benign ROI and BPH data show that 10/16 parameters as shown in Table 4 are statistically different for field effect. These ten FISH parameters were CEP10% Abnormal, CEP10% Gain, CEP7% Abnormal, CEP7% Gain, CEP8% Abnormal, CEP8% Gain, MYC % Gain, LPL % Abnormal, PTEN % Loss, and PTEN/CEP10% Loss.

TABLE 4 t-Test Comparing Benign and BPH

| FISH Parameters | Benign-Mean(Std) | BPH-Mean(Std) | p-value | Flag |
|---|---|---|---|---|
| CEP10 % Abnorm | 31.41(9.91) | 22.92(8.14) | 0.0038 | Significant |
| CEP10 % Gain | 5.25(4.44) | 2.31(4.72) | 0.0469 | Significant |
| CEP7 % Abnorm | 29.82(8.57) | 19.46(6.44) | <.0001 | Significant |
| CEP7 % Gain | 6.39(6.81) | 1.54(3.93) | 0.0139 | Significant |
| CEP8 % Abnorm | 31.37(12.92) | 23(6.02) | 0.0210 | Significant |
| CEP8 % Gain | 7.93(6.93) | 1.54(2.42) | 0.0017 | Significant |

TABLE 4-continued t-Test Comparing Benign and BPH

| FISH Parameters | Benign-Mean(Std) | BPH-Mean(Std) | p-value | Flag |
|---|---|---|---|---|
| CEP8 % Loss | 23.44(13) | 21.46(5.78) | 0.5611 | |
| MYC % Gain | 9.38(8.31) | 1.85(2.71) | 0.0019 | Significant |
| LPL % Abnorm | 32.15(12.45) | 22.69(8.58) | 0.0052 | Significant |
| LPL % Loss | 24.63(11.4) | 21.62(8.69) | 0.3312 | |
| PTEN % Loss | 34.29(16.86) | 20.92(8.6) | 0.0064 | Significant |
| PTEN/CEP10 % Loss | 17.71(16.47) | 7.85(4.86) | 0.0275 | Significant |
| CEP7/CEP10 % Gain | 16.65(10.26) | 12.15(5.36) | 0.1105 | |
| LPL/CEP8 % Loss | 11.73(9.45) | 8.08(4.18) | 0.1487 | |
| MYC/CEP8 % Gain | 13.44(12.84) | 7.77(4.25) | 0.0951 | |
| MYC/LPL % Gain | 13.97(11.64) | 8.08(4.75) | 0.0618 | |

The ten FISH parameters, which showed significant difference between BPH and tumor or benign ROI groups based on two-sample t-test, were selected for further evaluation. The ROC method was applied to identify the optimal cut-off value for these FISH parameters. Table 5 summarizes the sensitivity, specificity, and AUC for each of these ten FISH parameters in distinguishing tumor ROI with BPH, as well as distinguishing benign ROI with BPH. The top five FISH single parameters were selected based on their AUC values in distinguishing benign ROI specimens vs. BPH for field effect. They were PTEN/CEP10% Loss, PTEN % Loss, CEP7% Abnormal, MYC % Gain and CEP8% Gain, as shown in Table 5.

TABLE 5

Selection of the top five FISH single parameters

| FISH Parameters | Tumor—BPH | | | Benign—BPH | | |
|---|---|---|---|---|---|---|
| | Sensitivity | Specificity | AUC | Sensitivity | Specificity | AUC |
| CEP8 % Gain | 0.794 | 0.769 | 0.853 | 0.824 | 0.769 | 0.871 |
| MYC % Gain | 0.912 | 0.769 | 0.908 | 0.824 | 0.769 | 0.846 |
| CEP7 % Abnorm | 0.882 | 0.808 | 0.896 | 0.765 | 0.808 | 0.845 |
| PTEN % Loss | 0.588 | 0.808 | 0.726 | 0.706 | 0.808 | 0.827 |
| PTEN/CEP10 % Loss | 0.824 | 0.808 | 0.881 | 0.647 | 0.808 | 0.788 |
| CEP10 % Gain | 0.941 | 0.846 | 0.93 | 0.765 | 0.846 | 0.786 |
| CEP10 % Abnorm | 0.794 | 0.808 | 0.865 | 0.765 | 0.731 | 0.775 |
| CEP7 % Gain | 0.853 | 0.846 | 0.886 | 0.706 | 0.769 | 0.77 |
| CEP8 % Abnorm | 0.941 | 0.885 | 0.966 | 0.647 | 0.769 | 0.752 |
| LPL % Abnorm | 0.794 | 0.923 | 0.945 | 0.647 | 0.769 | 0.736 |

The top five single probe parameters were grouped in all possible combinations of four-probe sets, and then analyzed by Receiving Operating Characteristic (ROC curve) using SAS with cut-offs ranging from 5% to 35% by 1% on benign specimens for cut-off values, AUC, as well as the minimum DFI. For multi-probe combinations, varying cut-offs independently for each parameter generates a field of points on the graph, and the points with the highest sensitivity value at each specificity value are used to define the ROC curve. While statistical methods were used to generate possible combinations and cut-off values, scientific judgment was used to weigh the various trades-offs to result in the final decision of cut-off values and probe combinations.

The analysis in Table 6 showed that probe set 3 has the largest AUC of 0.938, while AUC of probe set 1 is the second largest of 0.917 with the least DFI, and best sensitivity and specificity. Probe set 3 has only one LSI probe, namely PTEN, while probe set 1 has two LSI probes, namely PTEN and MYC. CEP probes are used to detect aneusomy whereas LSI probes are generally used to detect deletion, duplication, or amplification of specific genes. Based on this analysis, probe set 1, including PTEN % loss, CEP7% Abnorm, MYC % gain, and CEP8% Gain, was selected. The corresponding sensitivity and specificity of probe set 1 are 0.882 and 0.846, respectively.

TABLE 6

ROC analysis of four-probe combinations from the top five single FISH parameters

| Probes | Probe Combination | Cut-Off 1 | Cut-Off 2 | Cut-Off 3 | Cut-Off 4 | DFI | Sens. | Spec. | AUC |
|---|---|---|---|---|---|---|---|---|---|
| Probe Set 1 | PTEN % Loss, CEP7 % Abnorm, MYC % Gain, CEP8 % Gain | 33 | 28 | 35 | 34 | 0.194 | 0.882 | 0.846 | 0.917 |
| Probe Set 2 | PTEN/CEP10 % Loss, CEP7 % Abnorm, MYC % Gain | 35 | 25 | 35 | N/A | 0.261 | 0.824 | 0.808 | 0.911 |
| Probe Set 3 | PTEN/CEP10 % Loss, CEP7 % Abnorm, CEP8 % Gain | 35 | 25 | 34 | N/A | 0.225 | 0.882 | 0.808 | 0.938 |
| Probe Set 4 | PTEN/CEP10 % Loss, MYC % Gain, CEP8 % Gain | 35 | 5 | 35 | N/A | 0.371 | 0.647 | 0.885 | 0.834 |

Figure 4:
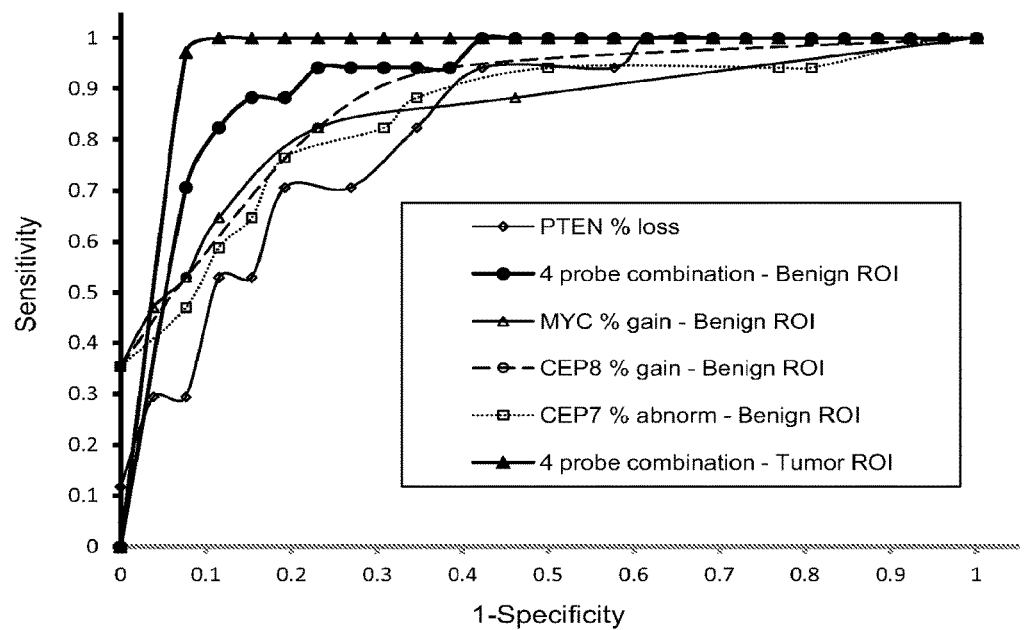
FIG. 4 is a graph of sensitivity vs. 1-specificity (ROC curve) for individual FISH parameters (PTEN % Loss, Cep 7% Abnorm, MYC % Gain, and CEP 8% Gain) and the four-probe combination. Data were calculated from the FISH evaluation of the 17 benign ROI and 26 BPH specimens. The ROC plot for the four-probe combination is based on the 33 tumor ROI and the 26 BPH specimens. The maximum AUC of the ROC curves are shown in the table.

ROC curves plot for the best four-probe combination and the four single FISH parameters, including PTEN % loss, CEP7% Abnorm, MYC % gain, CEP8% Gain, are shown in FIG. 4. Data were obtained from the FISH evaluation of the 17 benign ROI and 26 BPH specimens. The calculation of the four-probe combination of the 33 tumor ROI and 26 BPH specimens is also shown on the ROC plot. The AUCs of the ROC curves are shown in the table under the ROC plot.

Table 7 was the summary of 4-probe combination performance. The cut-off values chosen for four individual probe parameters were PTEN% loss>33, CEP7% Abnormal>28, MYC% gain>35, and CEP8% Gain>34. The sensitivity of 4-probe combination was 100% and specificity was 84.6% for tumor ROI vs. BPH. While comparing benign ROI with BPH, the probe combination yielded a sensitivity of 88.2% and a specificity of 84.6%.

TABLE 7

Summary of Four-Probe Combination with Cut-Offs

| | Tumor BPH** | | | Benign BPH** | | |
|---|---|---|---|---|---|---|
| FISH Parameter | Sensitivity | Specificity | AUC | Sensitivity | Specificity | AUC |
| Combination * | 1.000 | 0.846 | 0.960 | 0.882 | 0.846 | 0.917 |

* Combination: PTEN % Loss, CEP7 %Abnorm, MYC % Gain, CEP8 % Gain
**Cut-off 1 PTEN % Loss 33; Cut-off 2 CEP7 % Abnorm 28; Cut-off 3 MYC % Gain 35; Cut-off 4 CEP8 % Gain 34

ROC analysis shown in FIG. 5 further defined the cutoff range for each single FISH parameter of the probe set selected.

Comparing to PSA testing, sensitivity for patients with a serum PSA level above 4.0 ng/mL is about 20% in contemporary series, and the specificity of PSA testing is approximately 60% to 70% (Prostate-Specific Antigen Best Practice Statement, 2009 Update, American Urological Association). With FISH test using the 4-probe set selected in this study, 100% sensitivity and 84.6% specificity were achieved for tumor specimens. Thus, the FISH assay has the potential to outperform PSA test. With high sensitivity, a negative result can rule out the possibility of cancer, and further biopsy can be avoided. Moreover, PSA has poorer discriminating ability in men with symptomatic BPH (Meigs et al., J. Gen. Intern. Med. 11: 505 (1996)), while the FISH assay described herein has the potential to detect benign ROIs based on the field effect with a sensitivity of 88.2% and a specificity of 84.6%.

Another assay used for prostate cancer diagnosis is PCA3 test (Vlaeminck-Guillem et al., Urology 75: 447 (2010)). In four studies evaluating patients with indeterminate PSA (2.5 to 10.0 ng/mL), sensitivity ranged from 53 to 84 percent and specificity ranged from 71 to 80 percent. In three studies with at least 200 patients that provided data on PCA3 performance following a previous negative biopsy, sensitivity ranged from 47 to 58 percent, and specificity ranged from 71 to 72 percent. Although PCA3 has better performance than PSA in independently predicting a positive biopsy, the performance of the four-probe FISH assay described herein is better that both PSA and PCA3 tests, with 100% sensitivity and 84.6% specificity for tumor specimens, and 88.2% sensitivity and 84.6% specificity for benign ROIs.

In addition to the above, the FISH assay also can be used on cells from frozen specimens or cytology specimens. The evaluation includes signal detection via microscopy or image acquisition, signal enumeration, and subsequent data analysis algorithms. FISH assay uses stable DNA for detection of large chromosomal changes (deletion, amplification, aneusomy, and translocation), allows for molecular assessment to be combined with tissue morphology, can detect rare abnormalities in multi-focal and heterogeneous cancers, can detect the presence of cancer in a biopsy specimen that does not contain actual tumor as accessed by histological evaluation, can be used as a stand-alone test or as an adjunct to other tests (e.g., histology, PSA, nomogram, methylation, and mutation), and, by combining probes, enables an increase in sensitivity and specificity to be realized as compared to a single analyte assay.

The method may aid histological tissue evaluation to distinguish cancer from difficult benign conditions (BPH), to distinguish benign tissue from pre-cancerous lesions, and may aid in diagnosis of adenocarcinoma in biopsy, transurethral resection (TURP), or surgical (radical prostatectomy) specimens.

In this study with a RP specimen set, chromosomal abnormalities were observed within tumor regions as well as within regions of normal histology extending beyond histologically evident tumor, which confirmed field canceration effect of prostate cancer. The FISH detection of field canceration may reduce diagnostic biopsy sampling area by discovering chromosomal abnormalities in field cells apart from an existing cancer that was missed by the biopsy. Therefore, a molecular test based on FISH to measure MYC, CEP8, PTEN, and CEP7 may allow detection of cancer otherwise missed by histopathological examination and, thus, improve the diagnosis of prostate cancer by reducing sampling error of prostate needle biopsies.

Example 3

This example describes the analysis of prostate specimens with immunofluorescence (IF) and FISH using various combinations of probes.

The same FFPE prostate solid tumor tissue slides (Korac et al., J. Clin. Pathol. 58: 1336-1338 (2005)) were analyzed by immunoflourescence and FISH. A specimen pre-treatment/antigen retrieval protocol was developed and optimized for best results on the FFPE tissue.

The first step of this procedure was heat-induced epitope retrieval (HIER). FFPE slides were treated with Hemo-De (Scientific Safety Solvents, Keller, Tex.) for 10 minutes, D-limonene for 10 minutes, twice with 100% ethanol for two minutes, 85% ethanol for two minutes, 70% ethanol for two minutes, 50% ethanol for two minutes, 30% ethanol for two minutes, and water for five minutes. Afterwards, the slides were heated in sodium citrate buffer, pH 6.0, at 100° C. for 30 minutes, cooled down in sodium citrate buffer, pH 6.0, for 20 minutes, soaked in water for 5 minutes, and then soaked in phosphate-buffered saline (PBS) for five minutes.

The second step was IF using an anti-α-methylacyl-CoA racemase (AMACR) antibody (Zhong et al., Am. J. Clin. Pathol. 123: 231-236 (2005)) and the Tyramide Signal Amplification Assay (Sokolova et al., J. Molec. Diag. 9(5): 604-611 (2007)). The Tyramide Solution Assay kit and the Alexa Fluor 488 TSA™ (tyramide signal amplification) kit number 2 with horseradish peroxidase (HRP) (catalog no. T20912; Invitrogen, Carlsbad, Calif.; Molecular Probes, Eugene, Oreg.) were used in accordance with the manufacturer's directions. Endogenous peroxidase activity was blocked by incubation in 3% $H_2O_2$ for 30 minutes at room temperature. Blocking reagent (100 μL/slide) was added, and slides were incubated in a humidified box for 30 minutes at room temperature. Diluted anti-AMACR antibody (100 μL; rabbit; P504S; clone 13H4; Sigma, St. Louis, Mo.) (diluted in 1% blocking reagent at 1:100) was added, and the slides were incubated for one hour at room temperature. Slides were washed three times for five minutes in PBS/ 0.1% Tween 20. Stock HRP conjugate solution was diluted 1:100 in 1% blocking solution. A 100-μL volume of this working solution was sufficient to cover a standard 22×22 mm coverslip. The slides were incubated for 30 minutes at room temperature, washed three times for five minutes in PBS/0.1% Tween 20, and washed once in PBS. Tyramide solution (100 μL per slide) was added to each slide, and the slide was incubated for 10 minutes at room temperature in the dark. Slides were washed for five minutes in PBS and then washed for five minutes in Milli-Q water.

The third step was FISH. Slides were dehydrated in alcohol (70%, 85% and 100%, one minute each) and allowed to air-dry completely. Probe solution (10 μL) was added to each slide, and a coverslip was sealed over the slide with rubber cement. Probe and target DNA were co-denatured at 73° C. for five minutes and hybridized to slides overnight at 37° C. Coverslips were removed by soaking in 2×SSC/0.1% NP-40 at room temperature. Slides were washed in 2×SSC/0.3% NP-40 at 73° C. for 2 minutes, 2×SSC/0.1% NP-40 at room temperature for one minute, and then water, and allowed to air-dry completely in the dark. The slides were counterstained with DAPI.

Using Tyramide-mediated IF with anti-AMACR antibody in combination with PTEN (SpectrumOrange™) and CEP7® (SpectrumAqua™) FISH probes, seven specimens were processed and evaluated. AMACR is a specific marker for cancer cells. It is consistently over-expressed in prostate cancer epithelium. Its expression is also increased in pre-malignant lesions (prostatic intraepithelial neoplasia) (Zhong et al. (2005), supra). AMACR staining is strongly positive in the tumor ROI, indicating that AMACR protein is over-expressed. Most cells of this region only have one allele of PTEN by FISH assay, indicating a PTEN deletion, and two alleles of CEP 7, indicating that chromosome 7 is intact. The results of analysis of the seven specimens are shown in Table 8. The table shows that 12 out of 14 areas (12/14=85.7%) from seven specimens of the IF staining (AMACR positive+ or negative−) correlated with FISH signal abnormalities of the tested probes, as well as with the morphological assessment of tumor by a trained pathologist. In the heterogeneous and multifocal prostate cancer, AMACR antibody staining identified areas of interest for FISH evaluation.

TABLE 8

Immunofluorescence and FISH Analysis.

| Specimen | Slide Type | AMACR Status | FISH (PTEN or CEP7) |
|---|---|---|---|
| 23 | Tumor (inside scribed) area | + | Abnormal |
|  |  | + | Normal |
|  |  | − | Normal |
| 01 | Benign | − | Normal |
|  |  | + | Abnormal |
| 15 | Tumor | − | Normal |
| 03 | Tumor | + | Abnormal |
| 25 | Tumor (inside scribed area) | + | Abnormal |
|  |  | − | Normal |
|  | Tumor (outside scribed area) | + | Abnormal |
|  |  | − | Normal |
| 10 | Tumor (inside scribed area) | + | Abnormal |
|  | Tumor (outside scribed area) | + | Abnormal |
| 18 | Tumor | + | Normal |

Example 4

This example describes a method of histological sample pretreatment and hybridization for prostate cancer.

FFPE (formalin-fixed paraffin-embedded) histological specimens slides (sections) were baked at 56° C. for 2-24 hours, then were pretreated two to three times in Hemo-De (Scientific Safety Solvents) or Xyline for 5 to 10 minutes each at room temperature followed by two 1-minute rinses in 100% ethanol at room temperature, incubation in 45% formic acid/0.3% hydrogen peroxide for 15 minutes at room temperature, and a rinse in deionized water for 3-10 minutes. Slides were then incubated in pre-treatment solution (1×SSC, pH 6.3) at 80+/−5° C. for 35-50 minutes, rinsed for 3 minutes in deionized water, incubated 22+/−5 minutes in 0.15% pepsin in 0.1N HCl solution at 37° C., and rinsed again for 3 minutes in deionized water. Slides were dehydrated for 1 minute each in 70%, 85%, and 100% ethanol and then air dried. Ten microliters of each respective probe hybridization mix (LSI® buffer, blocking DNA, labeled probes) were added to the specimens, and a coverslip was applied and sealed with rubber cement. Slides were codenatured for 5 minutes at 73+/−2° C. and hybridized for 10-24 hours at 37° C. on a ThermoBrite (Vysis/Abbott Molecular, Inc.). Following hybridization, coverslips were removed. The sample was placed in a wash solution consisting of 0.3×-2×SSC & 0.3%-0.5% NP-40, and the temperature of the sample was raised to about 73° C. for about 2-5 minutes.

Then the support carrying the sample was counterstained with a nuclear DNA-binding stain, such as 4',6-diamidino-2-phenylindole (DAPI) either in solution, or upon drying the sample in the dark. In the latter case, the sample was counterstained with about 10 µL DAPI, and a new coverslip was placed over the sample. The sample was then viewed or stored, e.g., at about −20° C.

Example 5

This example describes a method of prostate FFPE slide IF-FISH procedure.

For the assay of simultaneous FISH and Immunofluorescence (IF) on the same FFPE prostate solid tumor tissue slides, a specimen pre-treatment/antigen retrieval protocol was developed and optimized for best results on the FFPE tissue for IF-FISH.

The first step of this procedure is antigen retrieval. Prostate cancer FFPE slides were baked at 56° C. for 2 hours to overnight. Slides were then de-paraffinized by two immersion in Hemo-De for 10 minutes each. Slides were then incubated in 100% ethanol for 2 minutes twice. Slides were hydrated by placement in 85%, 70%, 50%, and 30% ethanol for 2 minutes each. A final 5-minute immersion in molecular grade Milli-Q water was carried out. A water bath was pre-heated with a Coplin jar containing sodium citrate buffer (10 mM sodium citrate, 0.05% Tween 20, pH 6.0) until the temperature reached 96+/−4° C. Slides were incubated for 20-60 minutes. Slides were cooled at room temperature for 20-40 minutes on the bench. Slides were washed for five minutes in Milli-Q water and rinsed once for five minutes in PBS.

The second step is the immunoflorescence (IF) with AMACR antibody and Tyramide Signal Amplification Assay. The Tyramide Solution Assay (TSA) kit and the Alexa Fluor 488 TSA (tyramide signal amplification) kit number 2 (Invitrogen, Molecular Probes) were used following the manufacturer's directions. Endogenous peroxidase activity was blocked by incubation in 3% $H_2O_2$ for 30 minutes at room temperature. Blocking reagent (100 µL/slide) was added with incubation in a humidified box for 30 minutes at room temperature. Added were 100 uL of diluted AMACR rabbit antibody (diluted in 1% blocking reagent at 1:100) with incubation for 1 hour at room temperature. Slides were washed for five minutes three times in PBS/0.1% Tween 20. The stock HRP conjugate solution was diluted 1:100 in 1% blocking solution. A 100 µL volume of this working solution is sufficient to cover a standard 22×22 mm coverslip. The slides were incubated for 30 minutes at room temperature. Slides were washed for three times for five minutes each in PBS/0.1% Tween 20 and then washed once in PBS. Added were 100 µL of tyramide solution per slide followed by incubation for 10 minutes at room temperature in the dark. Slides were then washed for five minutes in PBS and five minutes in Milli-Q water.

The third step is FISH assay. Slides were dehydrated in alcohol (70%, 85% and 100%, one minute each), and allowed to air dry completely. Added were 10 µL of probe solution to each slide, and the coverslips were sealed over the slides with rubber cement. Probe and target DNA were denatured at 73° C. for 5 minutes followed by hybridization overnight at 37° C. The sample was placed in the wash solution consisting of 0.3×-2×SSC and 0.3%-0.5% NP-40, and the temperature of the sample was raised to about 73° C. for about 2-5 minutes. Then the support carrying the sample was counterstained with a nuclear DNA-binding stain, such as 4',6-diamidino-2-phenylindole (DAPI), either in solution or upon drying the sample in the dark. In the latter case, the sample was counterstained with about 10 µL DAPI, and a new coverslip was placed over the sample. The sample was then viewed or stored, e.g., at about −20° C.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:

1. A set of probes consisting of a locus-specific probe for MYC, a locus-specific probe for phosphatase and tensin homolog (PTEN), a centromeric probe for chromosome 8, a centromeric probe for chromosome 7, and optionally an anti-α-methylacyl-CoA racemase (AMACR) antibody, wherein each probe and the AMACR antibody is detectably labeled.

2. A kit comprising:
   (a) a set of probes that enables diagnosis of prostate cancer in a patient consisting of a locus-specific probe for MYC, a locus-specific probe for phosphatase and tensin homolog (PTEN), a centromeric probe for chromosome 8, and a centromeric probe for chromosome 7, wherein each probe is detectably labeled, and
   (b) instructions for diagnosing prostate cancer in a patient, wherein the instructions comprise determining in a sample of prostate cells obtained from the patient the presence of chromosomal abnormalities, wherein a MYC % gain (% gain is % of cells with MYC>2 signals) of greater than 35, a PTEN % loss (% loss is % of cells with <2 signals) of greater than 33, a chromosome 8% gain (% gain is % of cells with >2 signals) of greater than 34, and a chromosome 7% abnormal (% abnormal is % of cells with >2 or <2 signals) greater than 28 in a sample of prostate cells from a tumor region of interest (ROI) or a benign ROI of the prostate of the patient indicates that the patient has prostate cancer.

3. The kit of claim 2, which further comprises instructions for morphologically assessing a section of a prostate from a patient and identifying at least one tumor ROI, at least one benign ROI, or at least one tumor ROI and at least one benign ROI prior to determining the presence of chromosomal abnormalities.

4. The kit of claim 2, which further comprises instructions for assessing a section of a prostate from a patient by immunofluorescence and identifying the presence of a tumor ROI prior to determining the presence of chromosomal abnormalities.

5. The kit of claim 4, which further comprises a detectably labeled anti-α-methylacyl-CoA racemase (AMACR) antibody, and wherein the instructions for assessing a section of a prostate from a patient by immunofluorescence further comprise contacting the section with the detectably labeled anti-AMACR antibody and detecting over-expression of AMACR, wherein over-expression of AMACR in a region of the section indicates the presence of a tumor ROI.

6. The kit of claim 5, wherein the instructions further comprise treating the section with heat-induced epitope retrieval prior to assessing the section of a prostate from a patient by immunofluorescence.

7. The kit of claim 4, wherein the instructions further comprise treating the section with heat-induced epitope retrieval prior to assessing the section of a prostate from a patient by immunofluorescence.

8. The kit of claim 2, wherein the instructions comprise determining chromosomal abnormalities in a tumor ROI.

9. The kit of claim 2, wherein the instructions comprise determining chromosomal abnormalities in a benign ROI adjacent to a tumor ROI.

\* \* \* \* \*